(12) United States Patent
Van Rooijen et al.

(10) Patent No.: US 7,390,936 B1
(45) Date of Patent: Jun. 24, 2008

(54) COMMERCIAL PRODUCTION OF CHYMOSIN IN PLANTS

(75) Inventors: Gijs Van Rooijen, Calgary (CA); Keon Richard Glenn, Calgary (CA); Yin Shen, Calgary (CA); Joseph Boothe, Calgary (CA)

(73) Assignee: SemBioSys Genetics Inc., Calgary, Alberta (CA)

( * ) Notice: Subject to any disclaimer, the term of this patent is extended or adjusted under 35 U.S.C. 154(b) by 79 days.

(21) Appl. No.: 09/643,755

(22) Filed: Aug. 23, 2000

Related U.S. Application Data

(63) Continuation-in-part of application No. 09/378,696, filed on Aug. 23, 1999, now abandoned.

(51) Int. Cl.
*C12N 15/82* (2006.01)

(52) U.S. Cl. .................... 800/288; 800/287; 435/468

(58) Field of Classification Search ............... 800/287, 800/288, 295, 306; 435/172.1, 172.3, 69.8, 435/204; 536/25.5, 23.6, 22.1, 23.4, 24.1, 536/25.3
See application file for complete search history.

(56) References Cited

U.S. PATENT DOCUMENTS

| | | | |
|---|---|---|---|
| 4,666,847 | A | 5/1987 | Alford et al. |
| 5,139,943 | A | 8/1992 | Heinsohn et al. |
| 5,151,358 | A | 9/1992 | Heinsohn et al. |
| 5,215,908 | A | 6/1993 | Heinsohn et al. |
| 5,364,770 | A | 11/1994 | Berka et al. |
| 5,380,831 | A * | 1/1995 | Adang et al. |
| 5,543,576 | A | 8/1996 | van Ooijen et al. |
| 5,578,463 | A | 11/1996 | Berka et al. |
| 5,624,829 | A | 4/1997 | Sanders et al. |
| 5,714,474 | A | 2/1998 | Van Ooijen et al. |
| 5,716,807 | A | 2/1998 | Sanders et al. |
| 5,767,379 | A | 6/1998 | Baszczynski et al. |
| 5,804,694 | A | 9/1998 | Bruce et al. |
| 5,824,870 | A | 10/1998 | Baszczynski et al. |
| 5,863,759 | A | 1/1999 | Boel et al. |

FOREIGN PATENT DOCUMENTS

| | | |
|---|---|---|
| DE | 265 164 A1 | 2/1989 |
| EP | 0 134 662 A1 | 1/1992 |
| EP | 0 575 462 B1 | 12/1993 |
| EP | 0 477 277 B1 | 4/1995 |
| EP | 0 477 284 B1 | 8/1995 |
| WO | WO 90/15864 | 12/1990 |
| WO | WO 90/15865 | 12/1990 |
| WO | WO 90/15866 | 12/1990 |
| WO | WO 92/01042 | 1/1992 |
| WO | WO 92/18634 | 10/1992 |
| WO | WO 98/49326 | 11/1998 |

OTHER PUBLICATIONS (Buchanan, et al. Biochemistry & Molecular Biology of Plants (2000) American Society of Plant Physiologists, Rockville Md 20855, pp. 1024-1028, and Table 19.2, p1029).*
Buchanan, et al. Biochemistry & Molecular Biology of Plants (2000) American Society of Plant Physiologists, Rockville Mad 20855, pp. 1024-1028, and Table 19.2.*
Cramer et. al. (p. 95-118, , in Plant Biotechnology: New products and applications, 1999, ed. Hammond et. al., Springer, New York).*
Borisjik, et al., Nature Biotech, 1999 vol. 17, pp. 466-469,(submitted by Applicant).*
Komamytsky, et al, Plant Phys. 2000, vol. 124 pp. 927-933. (submitted by Applicant).*
Fischer, et al. Curr. Opin. Plant Biol. 2004, vol. 7, pp. 152-158 (submitted by Applicant).*
Kusnadi, et al. Biotech. Bioeng. 1998, vol. 60, No. 1, pp. 44-52 (submitted by Applicant).*
Oehler et al, 1999, Anal. Biochem.,vol. 268, No. 2, pp. 330-336. See PubMed print-out dated Sep. 12, 2006.*
Holzmann, 1994. Genetic Eng. News, vol. 14, No. 1, p. 34.*
Menhaus et. al. , 2004, Biotechnol. Prog. 2004, v. 220, pp. 1001-1014 (submitted by Applicant).*
Sardana et al. Synthesis of recombinant human cytokine GM-CSF in the seeds of transgenic tobacco plants. (1998) in Recombinant proteins from plants: production and isolation of clinically useful compounds; edited by Cunningham and Porter, pp. 77-87.*
Cullen et al. (1987) Bio/Technology 5:369-375.
Dunn-Coleman et al. (1991) Bio/Technology 9:976-981.
Foltman et al., (1977) Proc. Natl. Acad. Sci. USA 74:2331-2324.
Foltman et al., (1979) J. Biol. Chem. 254:8447-8456.
Harkki et al., (1989) Bio/Technology 7:596-603.
Nishimori et al. (1982) J. Biochem 91: 1085-1088.
Parente et al. (1991) FEMS 77: 243-250.
Pitts et al. (1991) Biochemical Society Transactions 19: 663-665.
Tsuchiya et al. (1993) Appl. Microbial Biotech. 40: 327-332.
van der Berg et al. (1990) Bio/Technology 8: 135-139.

* cited by examiner

*Primary Examiner*—Phuong Bui
*Assistant Examiner*—Cathy Kingdon Worley
(74) *Attorney, Agent, or Firm*—Bereskin & Parr; Micheline Gravelle

(57) ABSTRACT

A method for the commercial production of chymosin which involves the recombinant expression of chymosin in plant seeds, that enables chymosin to accumulate to at least 0.5% (w/w) of total seed protein is described. An improved method for the isolation of chymosin from the seed is also described.

11 Claims, 8 Drawing Sheets

FIGURE 1

```
  1 ATG AAC TTC CTT AAG TCT TTC CCT TTC TAC GCT TTC CTT TGT TTC GGT CAA TAC TTC GTT   60
  1  M   N   F   L   K   S   F   P   F   Y   A   F   L   C   F   G   Q   Y   F   V   20

60 GCT GTT ACT CAC GCT GCT GAG ATC ACC CGC ATT CCT CTC TAC AAA GGT AAG TCT CTC CGT  120
 21  A   V   T   H   A   A   E   I   T   R   I   P   L   Y   K   G   K   S   L   R   40

121 AAG GCG CTG AAG GAA CAT GGA CTT CTA GAA GAC TTC TTG CAG AAA CAA CAG TAT GGC ATC  180
 41  K   A   L   K   E   H   G   L   L   E   D   F   L   Q   K   Q   Q   Y   G   I   60

181 AGC AGC AAG TAC TCC GGC TTC GGT GAA GTT GCT AGC GTG CCA CTT ACC AAC TAC CTT GAT  240
 61  S   S   K   Y   S   G   F   G   E   V   A   S   V   P   L   T   N   Y   L   D   80

241 AGT CAA TAC TTT GGG AAG ATC TAC CTC GGA ACC CCG CCT CAA GAG TTC ACC GTT CTC TTT  300
 81  S   Q   Y   F   G   K   I   Y   L   G   T   P   P   Q   E   F   T   V   L   F  100

301 GAT ACT GGT TCC TCT GAC TTC TGG GTT CCC TCT ATC TAC TGC AAG AGC AAT GCC TGC AAG  360
101  D   T   G   S   S   D   F   W   V   P   S   I   Y   C   K   S   N   A   C   K  120

361 AAC CAC CAA AGA TTC GAT CCG AGA AAG TCG TCC ACC TTC CAG AAC TTA GGC AAA CCC TTG  420
121  N   H   Q   R   F   D   P   R   K   S   S   T   F   Q   N   L   G   K   P   L  140

420 TCT ATA CAC TAC GGT ACA GGT AGC ATG CAA GGA ATC TTA GGC TAT GAT ACC GTC ACT GTC  480
141  S   I   H   Y   G   T   G   S   M   Q   G   I   L   G   Y   D   T   V   T   V  160

481 TCC AAC ATT GTG GAC ATT CAA CAG ACA GTA GGA CTT AGC ACC CAA GAA CCA GGT GAT GTC  540
161  S   N   I   V   D   I   Q   Q   T   V   G   L   S   T   Q   E   P   G   D   V  180

541 TTC ACC TAT GCA GAA TTC GAT GGC ATC CTT GGT ATG GCA TAC CCA TCG CTC GCG TCA GAG  600
181  F   T   Y   A   E   F   D   G   I   L   G   M   A   Y   P   S   L   A   S   E  200

601 TAC TCG ATA CCT GTG TTT GAC AAC ATG ATG AAC CGA CAC CTA GTA GCT CAA GAC TTG TTC  660
201  Y   S   I   P   V   F   D   N   M   M   N   R   H   L   V   A   Q   D   L   F  220

661 TCG GTT TAC ATG GAC AGG AAT GGC CAG GAG AGC ATG CTC ACG CTT GGA GCT ATT GAT CCA  720
221  S   V   Y   M   D   R   N   G   Q   E   S   M   L   T   L   G   A   I   D   P  240

721 TCC TAC TAC ACA GGA TCT CTT CAC TGG GTT CCA GTC ACT GTG CAG CAG TAC TGG CAA TTC  780
241  S   Y   Y   T   G   S   L   H   W   V   P   V   T   V   Q   Q   Y   W   Q   F  260

781 ACT GTG GAC AGT GTC ACC ATC AGC GGT GTG GTT GTT GCA TGT GAA GGT GGA TGT CAA GCT  840
261  T   V   D   S   V   T   I   S   G   V   V   V   A   C   E   G   G   C   Q   A  280

841 ATC TTG GAT ACC GGT ACG TCC AAG CTG GTC GGA CCT AGC AGC GAC ATT CTC AAC ATT CAG  900
281  I   L   D   T   G   T   S   K   L   V   G   P   S   S   D   I   L   N   I   Q  300

901 CAA GCT ATT GGA GCC ACA CAG AAC CAG TAC GGT GAG TTT GAC ATA GAT TGC GAC AAC CTT  960
301  Q   A   I   G   A   T   Q   N   Q   Y   G   E   F   D   I   D   C   D   N   L  320

961 AGC TAC ATG CCT ACA GTT GTC TTT GAG ATC AAC GGC AAG ATG TAC CCA CTG ACC CCC TCC 1020
```

FIGURE 1 cont'd

```
321 S   Y   M   P   T   V   V   F   E   I   N   G   K   M   Y   P   L   T   P   S   340
1021 GCC TAT ACC AGC CAG GAT CAA GGG TTC TGC ACC AGT GGA TTC CAG AGT GAG AAC CAT TCC 1080
341 A   Y   T   S   Q   D   Q   G   F   C   T   S   G   F   Q   S   E   N   H   S   360

1081 CAG AAA TGG ATC TTG GGA GAT GTG TTC ATT CGT GAG TAC TAC AGC GTC TTT GAC AGG GCC 1140
361 Q   K   W   I   L   G   D   V   F   I   R   E   Y   Y   S   V   F   D   R   A   380

1141 AAC AAC CTC GTT GGG CTA GCT AAA GCA ATC TGA                                 1200
381 N   N   L   V   G   L   A   K   A   I   *                                    391
```

FIGURE 2

```
   1 ctgcaggaattcattgtactcccagtatcattatagtgaaagtttggctctctcgccggtggttttttacctctattta   80
  81 aagggttttccacctaaaaattctggtatcattctcactttacttgttactttaatttctcataatctttggttgaaat  160
 161 tatcacgcttccgcacacgatatccctacaaatttattatttgttaaacattttcaaaccgcataaaattttatgaagtc  240
 241 ccgtctatctttaatgtagtctaacattttcatattgaaatatataatttacttaattttagcgttggtagaaagcataa  320
 321 agatttattcttattcttcttcatataaatgtttaatatacaatataaacaaattctttaccttaagaaggatttcccat  400
 401 tttatattttaaaaatatatttatcaaatattttcaaccacgtaaatctcataataataagttgtttcaaaagtaataa  480
 481 aatttaactccataatttttttattcgactgatcttaaagcaacacccagtgacacaactagccatttttttctttgaat  560
 561 aaaaaaatccaattatcattgtatttttttatacaatgaaaatttcaccaaacaatcatttgtggtatttctgaagcaa  640
 641 gtcatgttatgcaaaattctataattcccatttgacactacggaagtaactgaagatctgcttttacatgcgagacacat  720
 721 cttctaaagtaattttaataatagttactatattcaagatttcatatatcaaatactcaatattacttctaaaaaattaa  800
 801 ttagatataattaaaatattactttttaattttaagtttaattgttgaatttgtgactattgatttattattctactat  880
 881 gtttaaattgttttatagatagtttaaagtaaatataagtaatgtagtagagtgttagagtgttaccctaaaccataaac  960
 961 tataacatttatggtggactaattttcatatatttcttattgcttttacctttcttggtatgtaagtccgtaactagaa 1040
1041 ttacagtgggttgccatggcactctgtggtcttttggttcatgcatgggtcttgcgcaagaaaaagacaaagaacaaga 1120
1121 aaaagacaaaacagagagacaaaacgcaatcacacaaccaactcaaattagtcactggctgatcaagatcgccgcgtcc 1200
1201 atgtatgtctaaatgccatgcaaagcaacacgtgcttaacatgcactttaaatggctcacccatctcaacccacacacaa 1280
1281 acacattgcctttttcttcatcatcaccacaaccacctgtatatattcattctcttccgccacctcaatttcttcacttc 1360
1361 aacacacgtcaacctgcatatgcgtgtcatcccatgcccaaatctccatgcatgttccaaccaccttctctcttatataa 1440
1441 tacctataaatacctctaatatcactcacttctttcatcatccatccatccagagtactactctctactactataatac 1520
1521 cccaacccaactcatattcaatactactctact ATG AAC TTC CTT AAG TCT TTC CCT TTC TAC GCT      1586
   1                                    M   N   F   L   K   S   F   P   F   Y   A     11

1587 TTC CTT TGT TTC GGT CAA TAC TTC GTT GCT GTT ACT CAC GCT GCT GAG ATC ACC CGC ATT   1646
  12  F   L   C   F   G   Q   Y   F   V   A   V   T   H   A   A   E   I   T   R   I    31

1647 CCT CTC TAC AAA GGT AAG TCT CTC CGT AAG GCG CTG AAG GAA CAT GGA CTT CTA GAA GAC   1706
  32  P   L   Y   K   G   K   S   L   R   K   A   L   K   E   H   G   L   L   E   D    51

1707 TTC TTG CAG AAA CAA CAG TAT GGC ATC AGC AGC AAG TAC TCC GGC TTC GGT GAA GTT GCT   1766
  52  F   L   Q   K   Q   Q   Y   G   I   S   S   K   Y   S   G   F   G   E   V   A    71

1767 AGC GTG CCA CTT ACC AAC TAC CTT GAT AGT CAA TAC TTT GGG AAG ATC TAC CTC GGA ACC   1826
  72  S   V   P   L   T   N   Y   L   D   S   Q   Y   F   G   K   I   Y   L   G   T    91
```

FIGURE 2 cont'd

```
1827 CCG CCT CAA GAG TTC ACC GTT CTC TTT GAT ACT GGT TCC TCT GAC TTC TGG GTT CCC TCT 1886
  92  P   P   Q   E   F   T   V   L   F   D   T   G   S   S   D   F   W   V   P   S  111

1887 ATC TAC TGC AAG AGC AAT GCC TGC AAG AAC CAC CAA AGA TTC GAT CCG AGA AAG TCG TCC 1946
 112  I   Y   C   K   S   N   A   C   K   N   H   Q   R   F   D   P   R   K   S   S  131

1947 ACC TTC CAG AAC TTA GGC AAA CCC TTG TCT ATA CAC TAC GGT ACA GGT AGC ATG CAA GGA 2006
 132  T   F   Q   N   L   G   K   P   L   S   I   H   Y   G   T   G   S   M   Q   G  151

2007 ATC TTA GGC TAT GAT ACC GTC ACT GTC TCC AAC ATT GTG GAC ATT CAA CAG ACA GTA GGA 2066
 152  I   L   G   Y   D   T   V   T   V   S   N   I   V   D   I   Q   Q   T   V   G  171

2067 CTT AGC ACC CAA GAA CCA GGT GAT GTC TTC ACC TAT GCA GAA TTC GAT GGC ATC CTT GGT 2126
 172  L   S   T   Q   E   P   G   D   V   F   T   Y   A   E   F   D   G   I   L   G  191

2127 ATG GCA TAC CCA TCG CTC GCG TCA GAG TAC TCG ATA CCT GTG TTT GAC AAC ATG ATG AAC 2186
 192  M   A   Y   P   S   L   A   S   E   Y   S   I   P   V   F   D   N   M   M   N  211

2187 CGA CAC CTA GTA GCT CAA GAC TTG TTC TCG GTT TAC ATG GAC AGG AAT GGC CAG GAG AGC 2246
 212  R   H   L   V   A   Q   D   L   F   S   V   Y   M   D   R   N   G   Q   E   S  231

2247 ATG CTC ACG CTT GGA GCT ATT GAT CCA TCC TAC TAC ACA GGA TCT CTT CAC TGG GTT CCA 2306
 232  M   L   T   L   G   A   I   D   P   S   Y   Y   T   G   S   L   H   W   V   P  251

2307 GTC ACT GTG CAG CAG TAC TGG CAA TTC ACT GTG GAC AGT GTC ACC ATC AGC GGT GTG GTT 2366
 252  V   T   V   Q   Q   Y   W   Q   F   T   V   D   S   V   T   I   S   G   V   V  271

2367 GTT GCA TGT GAA GGT GGA TGT CAA GCT ATC TTG GAT ACC GGT ACG TCC AAG CTG GTC GGA 2426
 272  V   A   C   E   G   G   C   Q   A   I   L   D   T   G   T   S   K   L   V   G  291

2427 CCT AGC AGC GAC ATT CTC AAC ATT CAG CAA GCT ATT GGA GCC ACA CAG AAC CAG TAC GGT 2486
 292  P   S   S   D   I   L   N   I   Q   Q   A   I   G   A   T   Q   N   Q   Y   G  311

2487 GAG TTT GAC ATA GAT TGC GAC AAC CTT AGC TAC ATG CCT ACA GTT GTC TTT GAG ATC AAC 2546
 312  E   F   D   I   D   C   D   N   L   S   Y   M   P   T   V   V   F   E   I   N  331

2547 GGC AAG ATG TAC CCA CTG ACC CCC TCC GCC TAT ACC AGC CAG GAT CAA GGG TTC TGC ACC 2606
 332  G   K   M   Y   P   L   T   P   S   A   Y   T   S   Q   D   Q   G   F   C   T  351

2607 AGT GGA TTC CAG AGT GAG AAC CAT TCC CAG AAA TGG ATC TTG GGA GAT GTG TTC ATT CGT 2666
 352  S   G   F   Q   S   E   N   H   S   Q   K   W   I   L   G   D   V   F   I   R  371

2667 GAG TAC TAC AGC GTC TTT GAC AGG GCC AAC AAC CTC GTT GGG CTA GCT AAA GCA ATC TGA 2726
 372  E   Y   Y   S   V   F   D   R   A   N   N   L   V   G   L   A   K   A   I   *  391

2727 agcttaataagtatgaactaaaatgcatgtaggtgtaagagctcatggagagcatggaatattgtatccgaccatgtaac 2806

2807 agtataataactgagctccatctcacttcttctatgaataaacaaaggatgttatgatatattaacactctatctatgca 2886

2887 ccttattgttctatgataaatttcctcttattattataaatcatctgaatcgtgacggcttatggaatgcttcaaatagt 2966
```

FIGURE 2 cont'd

```
2967 acaaaaacaaatgtgtactataagactttctaaacaattctaactttagcattgtgaacgagacataagtgttaagaaga 3046

3047 cataacaattataatggaagaagtttgtctccatttatatattatatattacccacttatgtattatattaggatgttaa 3126

3127 ggagacataacaattataaagagagaagtttgtatccatttatatattatatactacccatttatatattatacttatcc 3206

3207 acttatttaatgtctttataaggtttgatccatgatatttctaatattttagttgatatgtatatgaaagggtactattt 3286

3287 gaactctcttactctgtataaaggttggatcatccttaaagtgggtctatttaattttattgcttcttacagataaaaaa 3366

3367 aaaattatgagttggtttgataaaatattgaaggatttaaaataataataaataataaataacatataatatatgtatat 3446

3447 aaatttattataatataacatttatctataaaaaagtaaatattgtcataaatctatacaatcgtttagccttgctggac 3526

3527 gactctcaattatttaaacgagagtaaacatatttgacttttggttatttaacaaattattatttaacactatatgaaa 3606

3607 ttttttttttttatcggcaaggaaataaaattaaattaggagggacaatggtgtgtcccaatccttatacaaccaacttc 3686

3687 cacaggaaggtcaggtcggggacaacaaaaaaacaggcaagggaaattttttaatttgggttgtcttgtttgctgcataa 3766

3767 tttatgcagtaaaacactacacataaccctttagcagtagagcaatggttgaccgtgtgcttagcttcttttattttat 3846

3847 ttttttatcagcaaagaataaataaaataaaatgagacacttcagggatgtttcaacccttatacaaaaccccaaaaaca 3926

3927 agtttcctagcaccctaccaactaaggtacc                                                  3957
```

COMMERCIAL PRODUCTION OF CHYMOSIN IN PLANTS

This application is a continuation-in-part application of U.S. Ser. No. 09/378,696, filed on Aug. 23, 1999 now abandoned.

FIELD OF THE INVENTION

The present invention relates to improved methods for the recombinant production and isolation of chymosin from plants.

BACKGROUND OF THE INVENTION

Chymosin, also known as rennin, is a commercially important enzymatic protein, commonly used in the cheese manufacturing industry to coagulate milk. Traditionally chymosin has been prepared from its natural source, the fourth stomach of unweaned calves, although recovery from the stomachs of other mammals, such as lamb, goats etc. heretofore was known. More recently, primarily as a result of a decrease in calf production, recombinant DNA techniques have been employed to produce chymosin by fermentation in genetically engineered microorganisms. Thus a variety of bacterial and fungal hosts have been genetically modified to produce chymosin by fermentation, including for example, the bacterial hosts *Escherichia coli*, (European Patent 0 134 662 A1; Nishimori et al. (1982) J. Biochem 91: 1085-1088), *Bacillus subtilis* (U.S. Pat. No. 5,624,819; U.S. Pat. No. 5,716,807 and Parente et al. (1991) FEMS 77: 243-250) and the fungal hosts *Aspergillus* sp. (European Patent 0 575 462 B1; U.S. Pat. Nos. 5,364,770 and 5,863,759; Cullen et al. (1987) Bio/Technology 5: 369-375, Dunn-Coleman et al. (1991) Bio/Technology 9: 976-981., and Tsuchiua et al. (1993) Appl. Microbial Biotech. 40: 327-332), *Kluyveromyces lactis* (van der Berg et al. (1990) Bio/Technology 8: 135-139 and *Trichoderma ressei* (Jarkki et al. (1989) Bio/Technology 7: 596-603; Pitts et al. (1991) Biochemical Society Transactions 19: 663-665). As well, more general expression in fungi, yeast and bacteria (U.S. Pat. No. 4,666,847) and in filamentous fungi (U.S. Pat. No. 5,578,463).

The active enzyme chymosin (E.C. 3.4.23.4) is comprised of a polypeptide chain of a molecular mass of 35.6 kDa. However crude extracts of calf stomach mucosa in addition to active chymosin, contain two inactive precursor polypeptides known as pre-pro-chymosin and pro-chymosin. Pre-pro-chymosin contains an extra 58 amino acids at the N-terminus, whereas pro-chymosin contains an extra 42 amino acids. Conversion of the inactive precursor protein into enzymatically active chymosin requires the step-wise removal of the chymosin pre-peptide and pro-peptide. In vivo these activation steps take place in the calf stomach. The chymosin pre-peptide directs secretion of the polypeptide by the stomach cells and is removed upon secretion of the polypeptide by the stomach cells. The chymosin pro-peptide is subsequently removed in the gastric lumen, thereby activating the enzyme. The activation reaction can also be performed in vitro at pH values below 5. With regards to the enzyme chymosin, it should further be noted that chymosin purified from calf stomach is a mixture of two different polypeptides known as chymosin A and chymosin B. Both of these polypeptides are active and differ only with respect to one amino acid. The amino acid residue at position #290 is an aspartate residue in chymosin A and a glycine residue in chymosin B (Foltman et al., (1977) Proc. Natl. Acad. Sci. USA 74: 2331-2324; Foltman et al., (1979) J. Biol. Chem. 254: 8447-8456).

There are several disadvantages associated with the recombinant production of chymosin in fermentation systems. In general, fermentation systems require the use of large fermentation vessels that have both large space and energy requirements and consequently are costly. As well, the growth media require large volumes of water and may require special chemicals. Both of these may present environmental issues in the disposal of the large amounts of potentially harmful waste. Further, storage and shipment of raw material containing chymosin is problematic. The bacterial or fungal fermentation broth need to be processed immediately or refrigerated in large volumes since the enzyme is not stable for long periods in the broth.

The use of plants as bioreactors for the commercial production of recombinant proteins is well known. For example, avidin, β-glucuronidase and aprotinin (see patents U.S. Pat. Nos. 5,767,379, 5,804,694 and 5,824,870) have been recombinantly expressed in corn. Further, U.S. Pat. Nos. 5,543,576 and 5,714,474 are broadly directed to the recombinant production of enzymes in seeds and to the use of seeds or milled seeds comprising enzymes as a raw material in the preparation of food and feed products. Although U.S. Pat. Nos. 5,543,576 and 5,714,474 suggest chymosin as one potential enzyme that may be produced in seeds, there is no reduction to practice. These patents are further limited by the fact that in order to use the chymosin for the commercial production of cheese, chymosin would have to be purified from the seed or milled seeds.

PCT patent application WO 92/01042 discloses the expression of chymosin in the leaves of transgenic tobacco and potato plants. According to the disclosure chymosin expression levels of only 0.1% to 0.5% (w/w) of total soluble leaf protein were attained. The methodology of WO 92/01042 is further limited in that the production in leaves would require immediate extraction of the enzyme from the leaf material upon harvesting of the plants as the enzyme would lose activity when stored in leaves. In addition, due to the relatively high water content of leaves, large amounts of biomass must be processed.

There is a need in the art to further improve methods for the recombinant expression of chymosin in plants.

SUMMARY OF THE INVENTION

The present invention relates to novel and improved methods of producing commercial levels of chymosin in transgenic plants. The inventors have found that chymosin when expressed in the seeds of transgenic plants accumulates to levels of at least 0.5% (w/w) of total seed protein.

Accordingly, the invention provides a method for the production of chymosin in a plant seed comprising:

a) introducing into a plant cell a chimeric nucleic acid sequence molecule comprising in the 5' to 3' direction of transcription:

1) a first nucleic acid sequence capable of regulating transcription in said plant cell operatively linked to;
2) a second nucleic acid sequence encoding a chymosin polypeptide operatively linked to;
3) a third nucleic acid sequence capable of terminating transcription in said plant cell;

b) growing said plant cell into a mature plant capable of setting seed; and c) obtaining seed from the mature plant wherein said seed contains chymosin.

Preferably, at least 0.5% (w/w) of the total seed protein is chymosin.

The present invention also provides a method for the production of plant seeds containing at least 0.5% (w/w) chymosin in the total seed protein comprising:

(a) introducing into each of at least two plant cells a chimeric nucleic acid sequence molecule comprising in the 5' to 3' direction of transcription:
1) a first nucleic acid sequence capable of regulating transcription in said plant cell operatively linked to;
2) a second nucleic acid sequence encoding a chymosin polypeptide operatively linked to;
3) a third nucleic acid sequence capable of terminating transcription in said plant cell;

(b) growing each plant cell into a mature plant capable of setting seed;

(c) obtaining seed from each mature plant;

(d) detecting the levels of chymosin in the seed of each plant obtained in step (c) or in the seed of a plant generated from the seed of a plant obtained in step (c); and (e) selecting plants that contain at least 0.5% (w/w) chymosin in the total seed protein.

In preferred methods of the present invention, the nucleic acid sequence capable of regulating transcription is a seed-specific promoter. In further preferred methods, the chimeric nucleic acid sequence additionally comprises a signal sequence capable of targeting the chymosin polypeptide to the plant apoplast. In further preferred methods, the nucleic acid sequence encoding chymosin sequence is optimized for plant codon usage and the chymosin sequence further contains the chymosin pro-peptide or pre-pro-peptide or pre-peptide sequences.

In a further aspect, the present invention provides plant seeds expressing chymosin. In a preferred embodiment of the present invention, the plant seeds comprise a chimeric nucleic acid sequence comprising in the 5' to 3' direction of transcription:
1) a first nucleic acid sequence capable of regulating transcription in said plant cell operatively linked to;
2) a second nucleic acid sequence encoding a chymosin polypeptide operatively linked to;
3) a third nucleic acid sequence capable of terminating transcription in said plant cell wherein the seed contains chymosin.

Preferably, at least 0.5% (w/w) of the total seed protein is chymosin.

In another aspect the present invention provides plants capable of setting seed expressing chymosin. In a preferred embodiment of the invention, the plants capable of setting seed comprise a chimeric nucleic acid sequence comprising in the 5' to 3' direction of transcription:
1) a first nucleic acid sequence capable of regulating transcription in a plant cell operatively linked to;
2) a second nucleic acid sequence encoding a chymosin polypeptide operatively linked to;
3) a third nucleic acid sequence capable of terminating transcription in said plant cell, wherein the seed contains chymosin.

In yet another aspect the present invention provides a method for recovering chymosin from plant seeds. Accordingly, the present invention provides a method for obtaining chymosin from a plant seed comprising:

a) introducing into a plant cell a chimeric nucleic acid sequence molecule comprising in the 5' to 3' direction of transcription:
1) a first nucleic acid sequence capable of regulating transcription in said plant cell operatively linked to;
2) a second nucleic acid sequence encoding a chymosin polypeptide operatively linked to;
3) a third nucleic acid sequence capable of terminating transcription in said plant cell;

b) growing said plant cell into a mature plant capable of setting seed;

c) obtaining seed from the mature plant wherein said seed contains chymosin; and d) isolating said chymosin from said seed.

In preferred embodiments, isolation of chymosin from seed in step (d) comprises:
(i) crushing of the plant seed to obtain crushed plant seed;
(ii) contacting the crushed plant seed or a fraction thereof with a protein binding resin; and
(iii) recovering the chymosin from the protein binding resin.

In further preferred embodiments upon crushing of the plant seed the crushed seed material is fractionated into (a) an aqueous phase containing substantially all of the chymosin, (b) an oil fraction, and (c) a fraction containing the insoluble material insoluble material. Accordingly step (d) more preferably comprises:
(i) crushing of the plant seed to obtain crushed plant seed;
(ii) fractionating the crushed plant seed into an oil fraction, aqueous fraction and a fraction comprising insoluble material;
(iii) contacting the aqueous fraction with a protein binding resin; and
(iv) recovering the chymosin from the protein binding resin.

In a preferred embodiment, the protein binding resin is a hydrophobic interaction resin. In further preferred embodiments of the invention, the isolation of the chymosin further comprises the employment of an ion exchange resin and a hydrophobic interaction resin.

Other features and advantages of the present invention will become readily apparent from the following detailed description. It should be understood, however, that the detailed description and the specific examples while indicating preferred embodiments of the invention are given by way of illustration only, since various changes and modifications within the spirit and scope of the invention will become apparent to those skilled in the art of this detailed description.

BRIEF DESCRIPTION OF THE DRAWINGS

The invention will now be described in relation to the drawings in which:

FIG. 1 shows the nucleotide sequence (SEQ.ID.NO.:1) and corresponding amino acid sequence (SEQ.ID.NO.:2) of the open reading frame of a pre-pro-chymosin sequence. The "pre" sequence is indicated in Italics between and including amino acids 1 to 26. The "pre" sequence encodes a signal sequence identical to the PR-S signal sequence from tobacco sequence (Sijmons et al. (1990) Bio/technology 8: 217-221). Amino acids 27 to 67 inclusive are the "pro" sequence with the remaining amino acids encoding the mature chymosin polypeptide.

FIG. 2 shows the nucleotide sequence (SEQ.ID.NO.:3) of the phaseolin promoter- a pre-pro-chymosin-phaseolin terminator sequence responsible for the high levels of expression of chymosin in plant seeds.

DETAILED DESCRIPTION OF THE INVENTION

Figure 3:
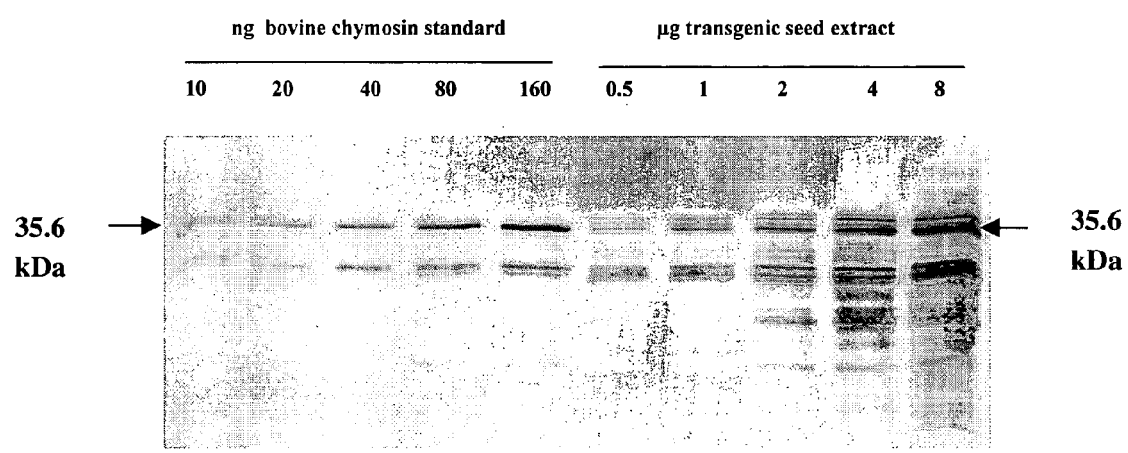
FIG. 3 is a Western blot analysis comparing a chymosin standard and a protein extract of seeds from a *Brassica* plant expressing chymosin.

As hereinbefore mentioned, the present invention relates to improved methods for the production of chymosin in transgenic plants. The present inventors have surprisingly found that by expressing chymosin in the seeds of plants, chymosin accumulation levels exceeding 0.5% (w/w) of total seed protein may be attained. These high expression levels in plant seeds allow significant commercial savings since the acreage of plants that needs to be grown can be limited and the amount of biomass that must to be subjected to extraction is reduced. The amount of biomass processed is further limited due to the relatively low water content present in plant seed. Furthermore, the expression in plants seed offers flexibility in storage and shipment of chymosin as a raw material,j since chymosin retains its enzymatic activity upon extraction from stored seed.

Accordingly, the invention provides a method for producing chymosin in plant seeds comprising:
 a) introducing into a plant cell a chimeric nucleic acid sequence molecule comprising in the 5' to 3' direction of transcription:
  1) a first nucleic acid sequence capable of regulating transcription in said plant cell operatively linked to;
  2) a second nucleic acid sequence encoding a chymosin polypeptide operatively linked to;
  3) a third nucleic acid sequence capable of terminating transcription in said plant cell;
 b) growing said plant cell into a mature plant capable of setting seed; and
 c) obtaining said seed from said mature plant wherein the seed contains chymosin.

In a preferred embodiment, at least 0.5% (w/w) of the total seed protein is chymosin. More preferably at least 1% (w/w) of the total seed protein is chymosin, even more preferably at least 2% (w/w) of the total seed protein is chymosin and most preferably at least 4% (w/w) of the total seed protein is chymosin.

As used herein the term "chymosin polypeptide" refers to all chymosins and includes pre-pro-chymosin and pro-chymosin polypeptides. The chymosin is preferably mammalian such as bovine, goat and sheep chymosin.

The term "nucleic acid sequence encoding a chymosin polypeptide" refers to all nucleic acid sequence encoding chymosin and all nucleic acid sequences that hybridize thereto under stringent hybridization conditions or would hybridize thereto but for the use of synonymous codons.

Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "nucleic acid sequence encoding a chymosin polypeptide" includes nucleic sequences that encode pre-pro-chymosin and pro-chymosin. In addition, the nucleic acid sequences that encode chymosin may be linked to additional nucleic acid sequences such as those that encode signal peptides.

In preferred embodiments of the present invention, nucleic acid sequences encoding bovine chymosin A or chymosin B are used (Moir et al. (1982) Gene 19: 127-138; Harris et al. (1982) Nucleic Acids Res. 10: 2177-2187). In further preferred embodiments nucleic acid sequences encoding chymosin are used which have been optimized for codon usage in plants. The natural bovine chymosin sequence has a GC content of 56% with a preference for a G or C in the third position of the codon. This differs from the codon bias for cattle which has an average GC content of 39% (Mishimori et al. (1982) J Biochem 91: 1085-1088). In a preferred embodiment, the codon usage of chymosin is manipulated to reflect a codon usage typical of seed-storage proteins found in oilseeds, for example using a GC content of 49% with a preference for a G or C in the third position of the codon (see Example 1).

The invention further includes the use of nucleic acid sequences encoding chymosin precursor proteins that can be activated, for example by treating the precursor polypeptide at low pH, to exhibit chymosin activity. Nucleic acid sequences encoding chymosin precursor proteins that may be used in accordance with the present invention include naturally occurring nucleic acid sequences encoding chymosin precursor proteins, such as "pro-chymosin", "pre-chymosin" and "pre-pro-chymosin", as well as non-naturally occurring nucleic acid sequences encoding precursor proteins comprising chymosin and capable of activation to exhibit chymosin activity. In a preferred embodiment of the invention, a nucleic acid sequence encoding bovine pro-chymosin comprising 42 extra amino acid residues is used (Moir et al. (1982) Gene 19: 127-138; Harris et al. (1982) Nucleic Acids Res. 10: 2177-2187). Other nucleic acid sequences encoding precursor proteins that may be used in accordance with the present invention include those encoding bovine pre-pro-chymosin comprising 58 extra amino acid residues (Moir et al. (1982) Gene 19: 127-138; Harris et al. (1982) Nucleic Acids Res. 10: 2177-2187), and nucleic acid sequences encoding plant signal sequences capable of targeting chymosin to a preferred subcellular compartment, for example the plant apoplast, the golgi apparatus or cytoplasm. In one preferred embodiment, the nucleic acid sequence encoding chymosin comprises a nucleic acid sequence encoding the tobacco pathogenesis related protein-S (PR-S) signal sequence (Sijmons et al. (1990) Bio/technology 8: 217-221) directing targeting to the plant apoplast linked to a nucleic acid sequence encoding a bovine pro-chymosin polypeptide sequence (FIG. 1 and SEQ.ID.1). Other naturally occurring signal sequences that could be used in accordance with the present invention include for example the barley alpha amylase signal sequence (Rogers (1985) J. Biol. Chem. 260(6): 3731-3738) directing targeting of the chymosin sequence to the apoplast. The nucleic acid sequences encoding additional peptide sequences may be homologous as well as heterologous with respect to the nucleic acid sequence encoding the chymosin polypeptide. The nucleic acid sequence encoding the additional peptide sequences, such as the pro-peptide, pre-propeptide or pre-peptide, may vary in length and are preferably codon-optimized for use in plants.

In embodiments of the invention involving the activation of a chymosin precursor protein, the activation reaction may be performed upon obtaining the plant seeds by for example treating an extracted seed fraction at low pH, preferably at pH values lower than 5, or the activation reaction may take place in planta. It is also possible to complete the activation reaction in a mixture comprising chymosin precursor polypeptides and enzymatically active chymosin. The chymosin precursor protein may be partially active or exhibiting no chymosin activity, however the precursor protein is typically not fully active.

Nucleic acid sequences encoding chymosin are readily available or obtainable by the skilled artisan based on chymosin nucleic acid sequences and/or amino acid sequences known in the art. The bovine nucleic acid and amino acid sequences for chymosin A and chymosin B for example, are known and may be directly used in accordance with the present invention. As well, the complete primary structure of lamb preprochymosin has been deduced from cDNA (Pungercar et al. (1990) Nucleic Acids Res. 18(15): 4602). These known chymosin nucleic acid sequences may also be used to design and construct probes to identify previously undiscovered nucleic acid sequences encoding chymosin. These probes may be used to isolate nucleic acid sequence encoding chymosin from for example cDNA or genomic libraries. The nucleic acid sequence encoding chymosin is preferably obtained from a mammal. Thus additional nucleic acid sequence chymosin sequences may be discovered and used in accordance with the present invention.

The term "nucleic acid sequence" as used herein refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

In accordance with the present invention, the chimeric nucleic acid sequences can be incorporated in a known manner in a recombinant expression vector which ensures good expression in a plant seed. Accordingly, the present invention includes a recombinant expression vector comprising a chimeric nucleic acid sequence of the present invention suitable for expression in a seed cell.

The term "suitable for expression in a seed cell" means that the recombinant expression vectors contain the chimeric nucleic acids sequence of the invention, a regulatory region and a termination region, selected on the basis of the seed cell to be used for expression, which is operatively linked to the nucleic acid sequence encoding the polypeptide of desirable amino acid composition. Operatively linked is intended to mean that the chimeric nucleic acid sequence encoding the polypeptide is linked to a regulatory sequence and termination region which allows expression in the seed cell. A typical construct consists, in the 5' to 3' direction of a regulatory region complete with a promoter capable of directing expression in a plant, a chymosin coding region and a transcription termination region functional in plant cells. These constructs may be prepared in accordance with methodology well known to those of skill in the art of molecular biology (see for example: Sambrook et al. (1990) Molecular Cloning, 2nd ed. Cold Spring Harbor Press). The preparation of constructs may involve techniques such as restriction digestion, ligation, gel electrophoresis, DNA sequencing and PCR. A wide variety of cloning vectors are available to perform the necessary cloning steps. Especially suitable for this purpose are the cloning vectors with a replication system that is functional in *Escherichia coli* such as pBR322, the pUC series M13 mp series, pACYC184, pBluescript etc. The nucleic acid sequence may be introduced into these vectors and the vectors may be used to transform *E. coli* which may be grown in an appropriate medium. Plasmids may be recovered from the cells upon harvesting and lysing the cells. Final constructs may be introduced into plant vectors compatible with integration into the plant such as the Ti and Ri plasmids.

The selection of regulatory sequences will determine the plant organ in which the protein is expressed and may influence the level that a gene will be transcribed. Regulatory sequences are art-recognized and are selected to direct expression in the plant cell. Accordingly, the term "regulatory sequence" includes promoters, enhancers, ribosome binding sites, introns and other expression elements. Examples of promoters include both non-seed specific, constitutive promoters such as the 35-S CaMV promoter (Rothstein et al. (1987) Gene 53: 153-161) and seed specific promoters such as the phaseolin promoter (Sengupta-Gopalan et al., (1985) PNAS USA 82: 3320-3324) or the *Arabidopsis* 18 kDa oleosin promoter (van Rooijen et al., (1992) Plant Mol. Biol. 18: 1177-1179). In preferred embodiments of the present invention, seed specific promoters are employed and more specifically the phaseolin promoter. Enhancers which may be used include the AMV leader (Jobling and Gehrke (1987) Nature 325: 622-625) to increase the expression levels. It should be understood that the design of the expression vector may depend on such factors as the choice of the plant species and/or the type of polypeptide to be expressed.

The region containing the transcriptional terminator sequence preferably includes from about 200 to about 1,000 nucleotide base pairs and may comprise any such sequences functional in plants, such as the nopaline synthase termination region (Bevan et al., (1983) Nucl. Acid. Res. 11: 369-385), the phaseolin terminator (Van der Geest et al., (1994) Plant J. 6(3): 413-423), the terminator for the octopine synthase gene of *Agrobacterium tumefaciens* or other similarly functioning elements. These transcription terminator regions can be obtained as described by An (1987) Methods in Enzym. 153: 292 or are already present in plasmids available from commercial sources such as ClonTech, Palo Alto, Calif. The choice of the appropriate terminator may have an effect of the rate of transcription. In preferred embodiments of the invention the phaseolin terminator is employed.

The expression vectors may also contain a marker gene. Marker genes comprise all genes that enable distinction of transformed plant cells from non-transformed cells, including selectable and screenable marker genes. Conveniently, a marker may be a resistance marker to a herbicide, for example, glyphosate or phosphinothricin, or to an antibiotic such as kanamycin, G418, bleomycin, hygromycin, chloramphenicol and the like, which confer a trait that can be selected for by chemical means. Resistance markers to a herbicide when linked in close proximity to the chymosin gene may be used to maintain selection pressure on a population of transgenic plants for those plants that have not lost the gene of interest. Screenable markers may be employed to identify transformants through observation. They include but are not limited to the beta-glucuronidase or uidA gene, a beta-lactamase gene or a green fluorescent protein (Niedz et al. (1995) Plant Cell Rep. 14: 403).

A variety of techniques are available for the introduction of nucleic acid sequences, in particular DNA, into plant host cells. For example, the chimeric DNA constructs may be introduced into host cells obtained from dicotelydenous plants, such as tobacco, and oleagenous species, such as *Brassica napus* using standard *Agrobacterium* vectors by a transformation protocol such as described by Moloney et al. (1989) Plant Cell Rep. 8: 238-242 or Hinchee et al. (1988) Bio/Technol. 6: 915-922; or other techniques known to those skilled in the art. For example, the use of T-DNA for transformation of plant cells has received extensive study and is amply described in EP 0 120 516, Hoekema et al., (1985), Chapter V In: The Binary Plant Vector System Offset-drukkerij Kanters BV, Alblasserdam); Knauf et al. (1983), Genetic Analysis of Host Expression by *Agrobacterium*, p. 245, In: Molecular Genetics of Bacteria-Plant Interaction, Puhler, A. ed. Springer-Verlag, NY); and An et al., (1985) EMBO J., 4: 277-284. *Agrobacterium* transformation may also be used to transform monocot plant species (U.S. Pat. No. 5,591,616).

Conveniently, explants may be cultivated with *Agrobacterium tumefaciens* or *Agrobacterium rhizogenes* to allow for the transfer of the transcription construct in the plant host cell. Following transformation using *Agrobacterium* the plant cells are dispersed into an appropriate medium for selection, subsequently callus, shoots and eventually plants are recovered. The *Agrobacterium* host will harbour a plasmid comprising the vir genes necessary for transfer of the T-DNA to plant cells. For injection and electroporation (see below) disarmed Ti-plasmids (lacking the tumour genes, particularly the T-DNA region) may be introduced into the plant cell.

The use of non-Agrobacterium techniques permits the use of constructs described herein to obtain transformation and expression in a wide variety of monocotyledenous and dicotelydenous plant species. These techniques are especially useful for transformation of plant species that are intractable in an *Agrobacterium* transformation system. Other techniques for gene transfer include particle bombardment (Sanford, (1988) Trends in Biotechn. 6: 299-302), electroporation (Fromm et al., (1985) PNAS USA, 82: 5824-5828; Riggs and Bates, (1986) PNAS USA 83: 5602-5606), PEG mediated DNA uptake (Potrykus et al., (1985) Mol. Gen. Genetics., 199: 169-177), microinjection (Reich et al., Bio/Techn. (1986) 4: 1001-1004) and silicone carbide whiskers (Kaeppler et al. (1990) Plant Cell Rep. 9: 415-418).

In a specific application such as to *B. napus*, the host cells targeted to receive recombinant DNA constructs typically will be derived from cotyledonary petioles as described by Moloney et al. (1989) Plant Cell Rep. 8: 238-242. Other examples using commercial oil seeds include cotyledon transformation in soybean explants (Hinchee et al., (1988) Bio/Technol. 6: 915-922 and stem transformation of cotton (Umbeck et al., (1987) Bio/Technol. 5: 263-266).

Following transformation, the cells, for example as leaf discs, are grown in selective medium. Once the shoots begin to emerge, they are excised and placed onto rooting medium. After sufficient roots have formed, the plants are transferred to soil. Putative transformed plants are then tested for presence of a marker. Southern blotting may be performed on genomic DNA using an appropriate probe, to show integration into the genome of the host cell.

Transformed plants grown in accordance with conventional agricultural practices, are allowed to set seed. See, for example, McCormick et al. (1986) Plant Cell Reports 5: 81-84. The chymosin expression level that is attained in accordance with the present invention, is generally expected to vary somewhat depending on the transformed plant that is assayed. As hereinbefore mentioned for the process to be economically attractive, a minimum expression level is required. The terms "commercial" and "commercial levels" as used herein denote an expression level wherein at least 0.5% (w/w) and more preferably more than 2% (w/w) and most preferably more than 4% (w/w) of total seed protein is chymosin. Preferably expression levels are determined using quantitative Western blotting using the methodology described in detail in Example 2. Accordingly, typically a variety of transformed plants are screened and the expression level of chymosin in seed is determined. It is expected that typically between 5 and 50 plants may need to be screened to identify at least one plant expressing commercial levels of chymosin. Seeds obtained from plants expressing commercial levels of chymosin (i.e. at least 0.5% (w/w) of the total seed protein) are selected for further propagation.

Accordingly, the present invention provides a method for the production of plant seeds containing at least 0.5% ((w/w) chymosin in the total seed protein comprising:

(a) introducing into each of at least two plant cells a chimeric nucleic acid sequence molecule comprising in the 5' to 3' direction of transcription:
   1) a first nucleic acid sequence capable of regulating transcription in said plant cell operatively linked to;
   2) a second nucleic acid sequence encoding a chymosin polypeptide operatively linked to;
   3) a third nucleic acid sequence capable of terminating transcription in said plant cell;

(b) growing each plant cell into a mature plant capable of setting seed;

(c) obtaining seed from each mature plant;

(d) detecting the levels of chymosin in the seed of each plant obtained in step (c) or in the seed of a plant generated from the seed of a plant obtained in step (c); and (e) selecting plants that contain at least 0.5% (w/w) chymosin in the total seed protein.

Chymosin activity can be assayed by spectrophotometric or fluorometric methods or by milk-clotting assays. In the milk-clotting assay, a diluted sample is added to a milk solution so that the final solution contains 8% skim milk and 0.05% $CaCl_2$ in water. The clotting time or flake point is measured as the time it takes for the thin film of milk to break into visible particles. The concentration of chymosin is determined by comparing to a linear standard plotted as clotting time in seconds against the chymosin concentration (Tsuchiya et al. (1993) Appl. Microbiol. Biotechnol. 40: 327-332).

Two or more generations of plants may be grown and either crossed or selfed to allow identification of plants and strains with desired phenotypic characteristics including production of the recombinant polypeptide. It may be desirable to ensure homozygosity in the plants to assure continued inheritance of the recombinant trait. Methods for selecting homozygous plants are well known to those skilled in the art of plant breeding and include recurrent selfing and selection and anther and mircospore culture. Homozygous plants may also be obtained by transformation of haploid cells or tissues followed by regeneration of haploid plantlets subsequently converted to diploid plants by any number of known means (e.g. treatment with colchicine or other microtubule disrupting agents).

The present invention also provides plant seeds expressing chymosin. In a preferred embodiment of the present invention the plant seeds comprise a chimeric nucleic acid sequence comprising in the 5' to 3' direction of transcription:

1) a first nucleic acid sequence capable of regulating transcription in said plant cell operatively linked to;

2) a second nucleic acid sequence encoding a chymosin polypeptide operatively linked to;

3) a third nucleic acid sequence capable of terminating transcription in said plant cell, wherein the seed contains chymosin.

In a further aspect the present invention provides plants capable of setting seed expressing chymosin. In a preferred embodiment of the invention, the plants capable of setting seed comprise a chimeric nucleic acid sequence comprising in the 5' to 3' direction of transcription:

1) a first nucleic acid sequence capable of regulating transcription in said plant cell operatively linked to;

2) a second nucleic acid sequence encoding a chymosin polypeptide operatively linked to;

3) a third nucleic acid sequence capable of terminating transcription in said plant cell, wherein the seed contains chymosin.

The methods disclosed in the present invention can be used over a broad range of plant species. Particularly preferred plant cells employed in accordance with the present invention include cells from the following plants: soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalafa (*Medicago sativa*), wheat (*Triticum* sp.), barley (*Hordeum vulgare*), oats (*Avena sativa* L.), sorghum (*Sorghum bicolor*), *Arabidopsis thaliana*, potato (*Solanum* sp.), flax/linseed (*Linum usitatissimum*), safflower (*Carthamus tinctorius*), oil palm (*Eleais guineeis*), groundnut (*Arachis hypogaea*), Brazil nut (*Bertholletia excelsa*) coconut (*Cocus nucifera*), castor (*Ricinus communis*), coriander (*Coriandrum sativum*), squash (*Cucurbita maxima*), jojoba (*Simmondsia chinensis*) and rice (*Oryza sativa*).

The invention also provides a method for recovering chymosin from a plant seed comprising:

a) introducing into a plant cell a chimeric nucleic acid sequence molecule comprising in the 5' to 3' direction of transcription:

1) a first nucleic acid sequence capable of regulating transcription in said plant cell operatively linked to;

2) a second nucleic acid sequence encoding a chymosin polypeptide operatively linked to;

3) a third nucleic acid sequence capable of terminating transcription in said plant cell;

b) growing said plant cell into a mature plant capable of setting seed;

c) obtaining seed from the mature plant wherein said seed contains chymosin; and d) isolating said chymosin from said seed.

In preferred embodiments, isolation of chymosin from seed comprises:

i) crushing the plant seed to obtain crushed plant seed;

ii) contacting the crushed plant seed or a fraction thereof with a protein binding resin; and iii) recovering chymosin from the protein binding resin.

The term "crushing" as used herein refers to any process or methodology to comminute seed and includes mechanical pressing, grinding, crushing processes and the like. Preferably the seeds are ground using a mill such as for example a colloid mill, a disk mill, a pin mill, an orbital mill, an IKA mill, a homogenizer or similar equipment. The selection of the crushing equipment depends inter alia on the throughput requirements and on the seed source. Typically the crushing conditions selected result in the breakage of individual seed cells. It is of importance however that the chymosin polypeptide remains intact. Crushing conditions that would substantially inactivate the enzyme are undesirable in the practice of the present invention. The crushing process practiced in accordance with the present invention permits the recovery of a crushed plants seeds comprising chymosin.

The crushing process may be carried out using dry seed. Preferably however the seeds are crushed in the presence of water or a buffer. Prior to, during or after the crushing process, additional water or a buffer may be employed to dilute the seed extract. Preferably the crushed seed fraction obtained is between 2 and 100 fold diluted relative to the original seed volume. Furthermore the salt concentration may be adjusted by the addition of extraneous salts or salt solutions to the crushed seeds. Accordingly, preferably the extraneous salt concentration of the crushed seed that is obtained is preferably between approximately 0.1M and 2M. Suitable salts to adjust the salt concentration in accordance with the present invention include sulfate salts for example sodium sulfate, magnesium sulfate, and ammonium sulfate; phosphate salts, for example sodium phosphate, magnesium phosphate and ammonium phosphate; chloride salts, for example sodium chloride and calcium chloride; and mixtures thereof. A preferred salt used in accordance with the present invention is sodium chloride.

Upon crushing of the seed it is generally preferable to prepare an aqueous fraction of the crushed plant seeds by the removal of the insoluble material and the oil fraction of the seed. The insoluble material is substantially insoluble or in an insoublized association with insoluble material produced upon crushing of the plant seed material. The insoluble material is either produced in the plant seed or may be associated with the plant seed in the form of insoluble aggregates including, seed hulls, fibrous material, carbohydrates or external contaminants such as soil particles and the like. The process permits the separation of soluble seed material from insoluble seed material. Any suitable methodology may use be accomplished using any methodology that allows the separation of the seed insoluble material from the soluble seed constituents, including for example gravitation based methods such as for example centrifugation or size exclusion based methods such as filtration. In a preferred embodiment of the present invention centrifugation is used. Centrifugation equipment that may be used in accordance with the present invention includes a tubular bowl centrifuge, a decantation centrifuge, a hydrocyclone, a disk stack centrifuge, and the like.

Removal of the oil fraction is particularly desirable when chymosin is produced in seeds comprising a relatively high oil content such as rapeseed, flax, sunflower seed and the like. Any suitable methodology may be used that allows the separation of the oil fraction from the aqueous fraction of the seed, including for example gravitation based methods such as for example centrifugation or size exclusion based methods such as filtration. In a preferred embodiment of the present invention centrifugation is used. Centrifugation equipment that may be used in accordance with the present invention includes a tubular bowl centrifuge, a decantation centrifuge, a hydrocyclone, a disk stack centrifuge, and the like.

Generally the solids are removed prior to the oil fraction, however in other embodiments of the invention the removal of insoluble seed constituents and the oil fraction is accomplished concomitantly using a gravity based method such as a 3-phase tubular bowl centrifuge or decanter or a size-exclusion based separation method.

In a further preferred embodiment selective precipitation of the crushed plant seed extract or fraction thereof may be performed prior to contacting the plant seed extract or fraction thereof with the protein binding resin. This selective precipitation step is preferably accomplished by selecting any conditions that allow the precipitation of at least 50% (w/w)

of the endogenous seed proteins while substantially all chymosin remains soluble. With the term "substantially all" it is meant that at least approximately 75% (w/w) of all chymosin remains soluble. In a more preferred embodiment at least 85% (w/w) of all chymosin remains soluble. In the most preferred embodiment at least approximately 90% (w/w) of all chymosin remains soluble. In preferred embodiments of the present invention precipitation is accomplished by adjusting the pH of the crushed seed extract. The pH of the crushed seed is preferably adjusted to a pH of less than approximately 5.5. More preferably the pH is adjusted to a pH of between approximately 1.5 and 3.5. Most preferably the pH is adjusted to a pH of approximately 2.0. Any suitable acid my be used to adjust the pH, such as hydrochloric acid, sulfuric acid, phosphoric acid and the like preferably having a pH of less than 2. The precipitation step may take place concomitantly with the crushing step. In preferred embodiments, the precipitation step is performed subsequent to the seed-crushing step. Furthermore the precipitation may be performed prior to or subsequent to either the removal of the insoluble material or removal of the oil fraction. It is preferred however to remove the insoluble material and the oil fraction prior to selective precipitation.

The term "protein binding resin" means any resin that is capable of binding to proteins, in particular chymosin. In a preferred embodiment, the protein binding resin is a hydrophobic interaction resin.

The present inventors have found that a hydrophobic interaction resin is particularly useful in isolating chymosin from plant seeds. A "hydrophobic interaction resin" refers to any protein compatible resin capable of differentially binding proteins present in a mixture of proteins, said differential binding occurring as a result of differences in hydrophobic characteristics of the proteins present in the mixture. Hydrophobic interaction resins are generally art-recognized and include for example sepharose resins having functional groups such as alkyl groups (e.g. butyl-sepharose, octyl-sepharose) and phenyl groups (e.g. phenyl-sepharose) and superose resins having functional groups such as alkyl groups and phenyl groups. The hydrophobic interaction resin may be used batch-wise or prepared for column chromatography.

In the practice of the present invention the crushed seed extract or a fraction thereof comprising chymosin is contacted with the hydrophobic interaction resin under conditions that will permit chymosin to bind to the hydrophobic interaction resin. Preferred binding conditions in accordance with the present invention are conditions of high ionic strength, for example 1M to 2M salt concentrations, e.g. 1.5M ammonium sulphate. Other salts that may be used in accordance with the present invention include sulfate salts for example magnesium sulfate; phosphate salts, for example sodium phosphate, magnesium phosphate and ammonium phosphate; chloride salts, for example sodium chloride and calcium chloride; and mixtures thereof. Once binding has been accomplished conditions are altered so that the bound substances are eluted differentially thus allowing the recovery of chymosin from the hydrophobic interaction column. Preferably the ionic strength is altered to accomplish elution, for example the ionic strength is reduced from 1.5 M to 0.5 M. The changes in conditions may be performed stepwise or gradually. Other elution methodologies that may be employed include reducing the eluent polarity for example using a glycol gradient up to 50%, adding chaotropic species such as urea, guanidine hydrochloride; the addition of detergents; changing pH or temperature.

In further preferred embodiments, chymosin is additionally purified by employing an ion exchange resin. An "ion exchange resin" refers to any protein compatible resinous material which is capable of binding charged compounds. Ion exchange columns are art recognized and include anion and cation exchange resins. These resins may be employed in a batch fashion or as a column. Preferred cation exchange columns for use in the present invention, include for example Pharmacia SP-Sphadex, Indion SP-2, IBF SP-Triacryl, IBF SP-Spherodex and the like. Preferred anion exchange resins in this regard are DEAE cellulose, IBF Q Spherodex, Pharmacia Q-Sephadex, Indion Q-2, IBF Q-Trisacryl and the like. In the practice of the present invention the aqueous solution of comprising chymosin is contacted with the ion-exchange resin under conditions at which the chymosin will bind to the resin. Whether chymosin binds to the resin depends on the pH of the aqueous solution, i.e. whether the pH is below or above the isoelectric point of chymosin (approximately 4.6). Accordingly, contacting the aqueous solution comprising chymosin under conditions at which chymosin will bind to the column refers to adjusting the pH of the solution above or below its isoelectric point so that it will bind to the selected resin. Binding of chymosin to the resin further depends on the ionic strength. Accordingly, the salt concentration may vary, for example a concentration of less than 250 mM NaCl may be used. In order to elute chymosin of the resin conditions are selected which permit the elution of chymosin from the resin, preferably the ion concentration is adjusted to elute the chymosin of the resin. For example the salt concentration may be adjusted to a concentration of 2M NaCl. The pH and salt concentration of the chymosin preparation thus recovered may be adjusted as desired. The ion exchange resin step may be employed either prior or after the hydrophobic interaction step.

Optionally the chymosin preparation may be concentrated using for example ultrafiltration or treated for longer-term preservation using any suitable preservation methodology. For example the chymosin preparation may be sterilized using methodologies such as filtration or ultrafiltration.

Optionally the chymosin preparation may be concentrated using for example ultrafiltration or treated for longer-term preservation using any suitable preservation methodology. For example the chymosin preparation may be sterilized using methodologies such as filtration or ultrafiltration.

The following non-limiting examples are illustrative of the present invention:

EXAMPLES

Example 1

Construction of a Plant Transformation Vector Comprising of a Chimeric Nucleic Acid Sequence Containing pre-pro-chymosin A pro-chymosin gene was re-synthesized from the bovine pro-chymosin to reflect the plant-preferred codons (See FIG. 1 and SEQ.ID.NOS.: 1 and 2). Amino acids 27 to 67 are the pro-peptide sequence and amino acids 68 to 390 are the mature chymosin polypeptide. A PR-S signal sequence was attached to the 5' end of the pro-chymosin gene by PCR fusion. The PRS sequence includes amino acids 1 to 26 in FIG. 1. The pre-pro-chymosin DNA fragment was fused in between a phaseolin promoter and the phaseolin terminator derived from the common bean *Phaseolus vulgaris* Slightom et al (1983) Proc. Natl. Acad Sc USA 80: 1897-1901). A complete sequence of the phaseolin promoter-preprochymosin-phaseolin terminator insert responsible for the expression of chymosin in plant seeds is shown in FIG. 2 and SEQ.ID.NO.:3. This insert was cloned into the PstI-KpnI sites of vector pSBS2004 and pSBS3000 and resulted in plasmids pSBS2151 and pSBS2165 respectively. pSBS2004 is a derivative from the *Agrobacterium* binary plasmid pCGN1559 (MacBride and Summerfield, 1990, Plant Molec. Biol. 14 269-276) in which, the CAMV 35S promoter-neomycin phosphotransferase gene-tumor morphology large locus 3' antibiotic selection cassette of pCGN1559 was replaced with parsley ubiquitin promoter-phosphinothricin acyltransferase gene-parsley ubiquitin termination sequence to confer resistance to the herbicide glufosinate ammonium. pSBS3000 is a derivative from the *Agrobacterium* binary plasmid pPZP221 (Hajdukiewicz et al., 1994, Plant Molec. Biol. 25: 989-994). In pSBS3000, the CaMV35S promoter-gentamycin resistance gene-CAMV 35S terminator of pPZP221 was replaced with parsley ubiquitin promoter-phosphinothricin acetyl transferase gene-parsley ubiquitin termination sequence to confer resistance to the herbicide glufosinate ammonium.

Example 2

Generation of Chymosin-Expressing Transgenic Plants

Plasmids pSBS2151 and pSBS2165 were electroporated into *Agrobacterium* strain EHA101 (Hood, et al (1986) J Badteriol 144: 732-743). *Agrobacterium* strain EHA101 (pSBS2151) was used to transform *Brassica napus*. The procedure for the transformation of *Brassica* has been essentially outlined in Moloney et al. (1989) Plant Cell Reports 8: 238-242, except phosphinothricin, at a concentration of 1 to 2 mg/L, was used as the selectable agent. *Agrobacterium* strain EHA101 (pSBS2165) was used to transform flax cv Mc Gregor. Flax transformation was performed essentially as described in Jordan and McHughen (1988) Plant cell reports 7: 281-284, except transgenic shoots were selected on 10 μM L-phosphinothricine instead of kanamycin.

Example 3

Expression Levels of Chymosin in *Brassica*

Physical characteristics of *Brassica napus* seed extracted chymosin were compared relative to commercially available bovine chymosin. The molecular weight of the two chymosin proteins was determined by gel electrophoresis on a 12% poly-acrylamide gel and Western blot analysis using a polyclonal rabbit antibody as shown in FIG. 3. Specified concentrations were loaded onto a 12% poly-acrylamide gel and transferred to a membrane. The membrane was probed with a polyclonal antibody raised against commercial available bovine chymosin and visualized using alkaline phosphatase. This polyclonal antibody is immunologically reactive with several bands in the transgenic seed extract. Bands of the same electroforetic mobility are found in the commercial bovine chymosin extract. This suggests that the majority of the pre-pro-chymosin in the seed extract has matured into chymosin. The lower molecular weight bands likely result from proteolytic digestion of the mature protein and the minor higher molecular weight bands could correspond to altered processed forms of either preprochymosin or prochymosin. The protein levels for chymosin in one of the *Brassica* plants analyzed is shown in FIG. 3. Seeds were ground in water to make a seed extract and the protein concentration was determined as described in Bradford (1976) Anal. Biochem. 72: 248-254. Different concentrations of the same seed extract were electrophoresed on a gel along with a bovine derived chymosin standard loaded with known concentrations. Western blot analysis was performed with a polyclonal rabbit antibody and visualized using alkaline phosphatase. Quantitative densitometry was used to correlate the density of the 35.6 kDa band to the concentration of the protein by comparison with a standard curve derived from known concentrations of chymosin. Table 1 is a compilation of the data for the amount of chymosin in the identical seed extract of differing concentrations and resulting percent of expression. The slightly different levels reflect a standard error. Note that no data is provided for 4 μg and 8 μg of seed extract as the results exceeded the saturation range of the densitometer.

The biological activity of the plant (Brassica) derived chymosin was determined through the use of milk-clotting assays. In the milk-clotting assay, a diluted seed extract sample is added to a clotting substrate as described in (Tsuchiya et al. (1993) Appl. Microbiol. Biotechnol. 40: 327-332). Transgenic *Brassica* seeds had the ability to clot milk whereas, seeds that were not transformed with the pro-chymosin gene were unable to clot milk.

Example 4

Expression Levels of Chymosin in Flax (*Linum usitatissimum*)

Figure 4:
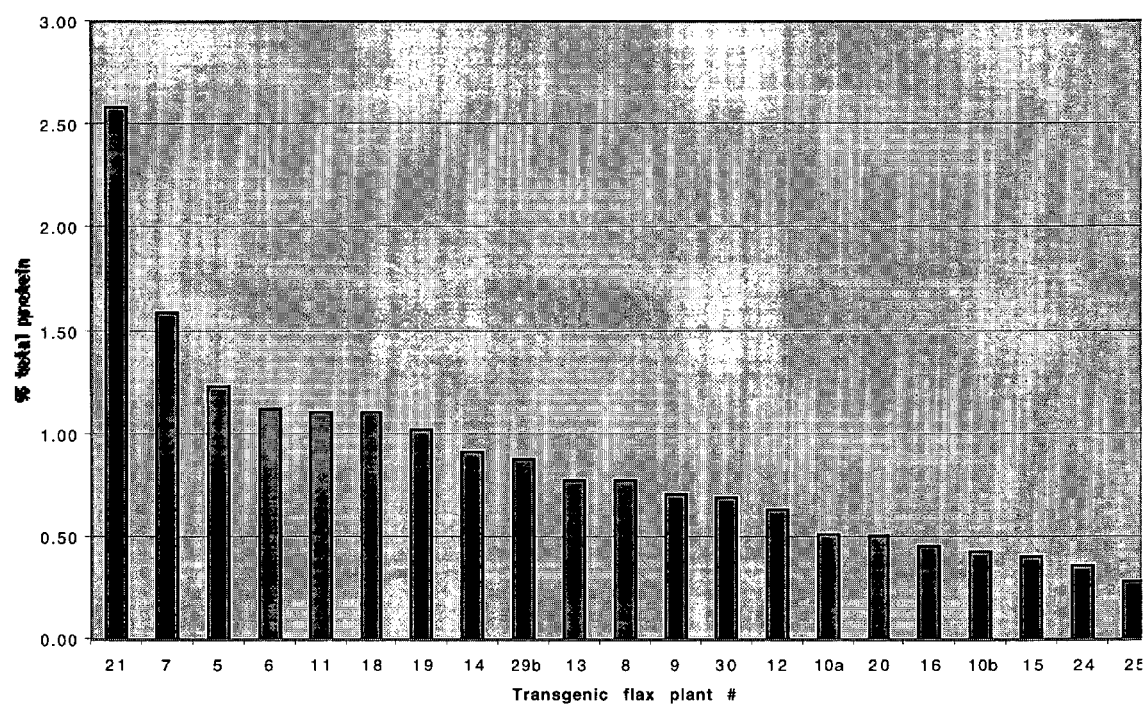
FIG. 4 is a bar diagram showing the expression of chymosin in flax seeds derived from independent transformed flax plants.

Transgenic flax plants containing the preprochymosin gene were analyzed for the presence of biologically active chymosin. The biological activity of the plant derived chymosin was determined through the use of milk-clotting assays. In the milk-clotting assay, a diluted flax seed extract sample is added to a clotting substrate as described in (Tsuchiya et al. (1993) Appl. Microbiol. Biotechnol. 40: 327-332). The clotting time or flake point is measured as the time it takes for the thin film of milk to break into visible particles. The concentration of chymosin in the seed extract is determined by comparing it to a linear standard curve plotted as clotting time in seconds against the chymosin concentration (Tsuchiya et al. (1993) Appl. Microbiol. Biotechnol. 40: 327-332). The chymosin concentration was first determined as a weight percentage of seed weight (=W %). The percentage chymosin as a percentage of total seed protein was calculated by using the formula (W/percentage protein in dry seed) X 100. For flax the total amount of protein as a percentage of seed weight equals approximately 20% (Gill, 1987, Linseed, Indian Council of Agricultural Research Publication). W×5 equals the expression level of chymosin as a percentage of total seed protein. FIG. 4 shows the expression levels of chymosin in transgenic flax seeds as a percentage of total protein for selected transformants.

Example 5

Purification of Chymosin from Transgenic *Brassica napus* Seed

Figure 5:
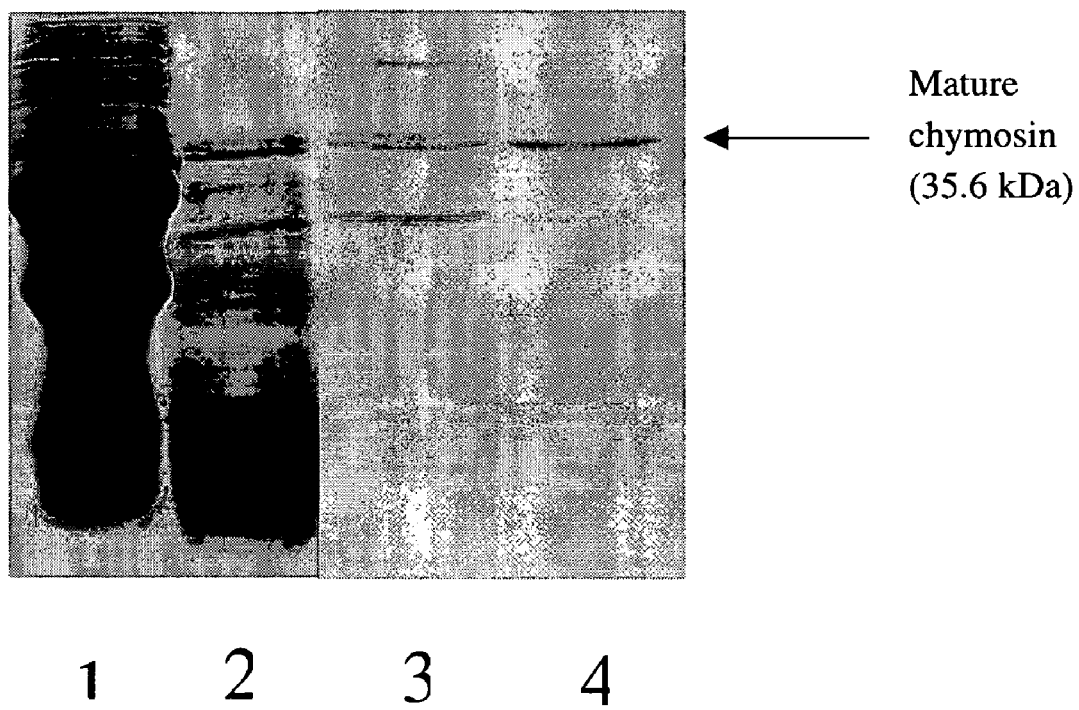
FIG. 5 shows a SDS-polyacrylamide gel showing progressive purification of chymosin obtained from transgenic seeds of *Brassica napus* as described in example 5.

This example describes the laboratory-scale purification of chymosin from transgenic seed produced as described in example 2. Forty grams of transgenic *Brassica napus* seed containing recombinant chymosin was combined with 400 mls of a solution containing 250 mM NaCl. The mixture was ground using a polytron to produce a slurry releasing the chymosin into solution. This slurry was then centrifuged at approximately 10,000×g to separate it into three phases, a solid pellet phase of insoluble material, an upper phase of seed oil bodies and associated proteins and a middle aqueous phase containing the chymosin, soluble seed proteins and other soluble seed components. Following centrifugation, the aqueous phase was removed and clarified by filtration. The clarified extract was adjusted to a pH of 2.0 by addition of sulfuric acid and allowed to sit for several minutes and then readjusted to pH 5.6 with aqueous ammonia. The extract was then centrifuged at 10,000×g to remove precipitated proteins and the soluble supernatant phase recovered. The low pH-treated extract was diluted with water to a conductivity of approximately 9.5 mmohs and then loaded on to an anion exchange column containing approximately 30 mls of DEAE-cellulose previously equilibrated with 0.5% sodium benzoate, 0.379% NaCl, pH 5.6. After loading, the column was washed with approximately 200 mls of 0.5% sodium benzoate, 0.379% NaCl, pH 5.6 and then eluted with 110 mls of 0.5% sodium benzoate, 10% NaCl, pH 5.6. The eluate from the anion exchange step was loaded on to a gel filtration column containing G25 sephadex (Amersham-Pharmacia) equilibrated with 25 mM sodium phosphate, 1 M ammonium sulfate, pH 5.6. Fifty mls of the eluate from this column was passed through a 0.22 um filter and then loaded on to a hydrophobic interaction column containing 4.6 mls of butyl sepharose (Fast Flow, Amersham-Pharmacia) previously equilibrated with 25 mM sodium phosphate, 1 M ammonium sulfate, pH 5.6. After loading, the column was washed with 20 mls of 25 mM sodium phosphate, 1 M ammonium sulfate, pH 5.6 followed by 75 mls of 25 mM sodium phosphate, 0.55 M ammonium sulfate, pH 5.6. Purified chymosin was eluted from the column with 24 mls of 25 mM sodium phosphate, 0.1 M ammonium sulfate, pH 5.6. FIG. 5 shows a SDS-polyacrylamide gel showing progressive purification of chymosin obtained from transgenic seeds of *Brassica napus* as described above. Lane 1, aqueous phase from total seed extract; lane 2 pH-treated extract; lane 3, DEAE-cellulose eluate; lane 4, purified chymosin eluted from butyl sepharose.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| | | | |
|---|---|---|---|
| mg of seed extract | 0.5 | 1.0 | 2.0 |
| ng of pro-chymosin in seed extract | 21 | 47 | 88 |
| level of expression (% of protein) | 4.2 | 4.7 | 4.4 |
| Average level of expression (% of protein) | | 4.43 | |

We claim:

1. A method for the production and isolation of chymosin in a plant seed comprising an oil fraction said method comprising:

a) introducing into a plant cell a chimeric nucleic acid molecule comprising in the 5' to 3' direction of transcription:

1) a seed-specific promoter capable of regulating transcription in said plant cell operatively linked to;

2) a second nucleic acid sequence encoding a chymosin polypeptide and comprising SEQ ID NO:1 operatively linked to;

3) a third nucleic acid sequence capable of terminating transcription in said plant cell;

b) growing said plant cell into a mature plant capable of setting seed wherein said seed contains chymosin;

c) obtaining seed from the mature plant wherein the seed contains at least 0.5% (w/w) chymosin; and d) isolating said chymosin from said seed using a method comprising:

(i) crushing the plant seed in the presence of water or a buffer to obtain crushed plant seed;

(ii) fractionating the crushed plant seed into an oil fraction, aqueous fraction and a fraction comprising insoluble material;

(iii) contacting the aqueous fraction with a protein binding resin; and (iv) recovering chymosin from the protein biding resin such that said chymosin is purified and biologically active.

2. The method according to claim 1 wherein said seed-specific promoter is a phaseolin promoter.

3. The method according to claim 1 wherein said third nucleic acid sequence is a phaseolin terminator.

4. The method according to claim 1 wherein said plant is selected from the group of plants consisting of soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalfa (*Medicago sativa*), wheat (*Triticum* sp.), barley (*Hordeum vulgare*), oats (*Avena sativa* L.), sorghum (*Sorghum bicolor*), *Arabidopsis thaliana*, potato (*Solanum* sp.), flax/linseed (*Linum usitatissimum*), safflower (*Carthamus tinctorius*), oil palm (*Eleais guineeis*), groundnut (*Arachis hypogaea*), Brazil nut (*Bertholletia excelsa*) coconut (*Cocus nucifera*), castor (*Ricinus communis*), coriander (*Coriandrum sativum*), squash (*Cucurbita maxima*), jojoba (*Simmondsia chinensis*) and rice (*Oryza sativa*).

5. The method according to claim 1 wherein at least 1% (w/w) of total seed protein of said seed is chymosin.

6. The method according to claim 1 wherein at least 2% (w/w) of total seed protein of said seed is chymosin.

7. The method according to claim 1 wherein at least 4% (w/w) of total seed protein of said seed is chymosin.

8. A method for the production of plant seeds comprising an oil fraction containing at least 0.5% (w/w) chymosin in the total seed protein and the isolation of the chymosin from the seeds comprising:
   (a) introducing into each of at least two plant cells a chimeric nucleic acid molecule comprising in the 5' to 3' direction of transcription:
      1) a seed-specific promoter capable of regulating transcription in said plant cell operatively linked to;
      2) a second nucleic acid sequence encoding a chymosin polypeptide and comprising SEQ ID NO:1 operatively linked to;
      3) a third nucleic acid sequence capable of terminating transcription in said plant cell;
   (b) growing each plant cell into a mature plant capable of setting seed;
   (c) obtaining seed from each mature plant;
   (d) measuring the levels of chymosin in the seed of each plant obtained in step (c) or in the seed of a plant generated from the seed of a plant obtained in step (c);
   (e) selecting plants that contain at least 0.5% (w/w) chymosin in the total seed protein; and
   (f) isolating said chymosin from said seed using a method comprising:
      (i) crushing the plant seed in the presence of water or a buffer to obtain crushed plant seed;
      (ii) fractionating the crushed the plant seed into an oil fraction, aqueous fraction and a fraction comprising insoluble material;
      (iii) contacting the aqueous fraction with a protein binding resin; and
      (iv) recovering chymosin from the protein binding resin such that said chymosin is purified and biologically active.

9. A method according to claim 1 wherein said protein binding resin is a hydrophobic interaction resin.

10. A method according to claim 8 wherein said protein binding resin is a hydrophobic interaction resin.

11. A method according to claim 10 further comprising using an ion exchange resin to further purify the chymosin.

* * * * *

SEQUENCE LISTING

```
<160> NUMBER OF SEQ ID NOS: 4

<210> SEQ ID NO 1
<211> LENGTH: 1173
<212> TYPE: DNA
<213> ORGANISM: Bovine
<220> FEATURE:
<221> NAME/KEY: CDS
<222> LOCATION: (1)..(1173)

<400> SEQUENCE: 1 atg aac ttc ctt aag tct ttc cct ttc tac gct ttc ctt tgt ttc ggt     48
Met Asn Phe Leu Lys Ser Phe Pro Phe Tyr Ala Phe Leu Cys Phe Gly
 1               5                  10                  15 caa tac ttc gtt gct gtt act cac gct gct gag atc acc cgc att cct     96
Gln Tyr Phe Val Ala Val Thr His Ala Ala Glu Ile Thr Arg Ile Pro
             20                  25                  30 ctc tac aaa ggt aag tct ctc cgt aag gcg ctg aag gaa cat gga ctt    144
Leu Tyr Lys Gly Lys Ser Leu Arg Lys Ala Leu Lys Glu His Gly Leu
         35                  40                  45 cta gaa gac ttc ttg cag aaa caa cag tat ggc atc agc agc aag tac    192
Leu Glu Asp Phe Leu Gln Lys Gln Gln Tyr Gly Ile Ser Ser Lys Tyr
     50                  55                  60 tcc ggc ttc ggt gaa gtt gct agc gtg cca ctt acc aac tac ctt gat    240
Ser Gly Phe Gly Glu Val Ala Ser Val Pro Leu Thr Asn Tyr Leu Asp
 65                  70                  75                  80 agt caa tac ttt ggg aag atc tac ctc gga acc ccg cct caa gag ttc    288
Ser Gln Tyr Phe Gly Lys Ile Tyr Leu Gly Thr Pro Pro Gln Glu Phe
                 85                  90                  95 acc gtt ctc ttt gat act ggt tcc tct gac ttc tgg gtt ccc tct atc    336
Thr Val Leu Phe Asp Thr Gly Ser Ser Asp Phe Trp Val Pro Ser Ile
            100                 105                 110
```

```
tac tgc aag agc aat gcc tgc aag aac cac caa aga ttc gat ccg aga       384
Tyr Cys Lys Ser Asn Ala Cys Lys Asn His Gln Arg Phe Asp Pro Arg
            115                 120                 125 aag tcg tcc acc ttc cag aac tta ggc aaa ccc ttg tct ata cac tac       432
Lys Ser Ser Thr Phe Gln Asn Leu Gly Lys Pro Leu Ser Ile His Tyr
    130                 135                 140 ggt aca ggt agc atg caa gga atc tta ggc tat gat acc gtc act gtc       480
Gly Thr Gly Ser Met Gln Gly Ile Leu Gly Tyr Asp Thr Val Thr Val
145                 150                 155                 160 tcc aac att gtg gac att caa cag aca gta gga ctt agc acc caa gaa       528
Ser Asn Ile Val Asp Ile Gln Gln Thr Val Gly Leu Ser Thr Gln Glu
            165                 170                 175 cca ggt gat gtc ttc acc tat gca gaa ttc gat ggc atc ctt ggt atg       576
Pro Gly Asp Val Phe Thr Tyr Ala Glu Phe Asp Gly Ile Leu Gly Met
            180                 185                 190 gca tac cca tcg ctc gcg tca gag tac tcg ata cct gtg ttt gac aac       624
Ala Tyr Pro Ser Leu Ala Ser Glu Tyr Ser Ile Pro Val Phe Asp Asn
            195                 200                 205 atg atg aac cga cac cta gta gct caa gac ttg ttc tcg gtt tac atg       672
Met Met Asn Arg His Leu Val Ala Gln Asp Leu Phe Ser Val Tyr Met
    210                 215                 220 gac agg aat ggc cag gag agc atg ctc acg ctt gga gct att gat cca       720
Asp Arg Asn Gly Gln Glu Ser Met Leu Thr Leu Gly Ala Ile Asp Pro
225                 230                 235                 240 tcc tac tac aca gga tct ctt cac tgg gtt cca gtc act gtg cag cag       768
Ser Tyr Tyr Thr Gly Ser Leu His Trp Val Pro Val Thr Val Gln Gln
            245                 250                 255 tac tgg caa ttc act gtg gac agt gtc acc atc agc ggt gtg gtt gtt       816
Tyr Trp Gln Phe Thr Val Asp Ser Val Thr Ile Ser Gly Val Val Val
            260                 265                 270 gca tgt gaa ggt gga tgt caa gct atc ttg gat acc ggt acg tcc aag       864
Ala Cys Glu Gly Gly Cys Gln Ala Ile Leu Asp Thr Gly Thr Ser Lys
            275                 280                 285 ctg gtc gga cct agc agc gac att ctc aac att cag caa gct att gga       912
Leu Val Gly Pro Ser Ser Asp Ile Leu Asn Ile Gln Gln Ala Ile Gly
    290                 295                 300 gcc aca cag aac cag tac ggt gag ttt gac ata gat tgc gac aac ctt       960
Ala Thr Gln Asn Gln Tyr Gly Glu Phe Asp Ile Asp Cys Asp Asn Leu
305                 310                 315                 320 agc tac atg cct aca gtt gtc ttt gag atc aac ggc aag atg tac cca      1008
Ser Tyr Met Pro Thr Val Val Phe Glu Ile Asn Gly Lys Met Tyr Pro
            325                 330                 335 ctg acc ccc tcc gcc tat acc agc cag gat caa ggg ttc tgc acc agt      1056
Leu Thr Pro Ser Ala Tyr Thr Ser Gln Asp Gln Gly Phe Cys Thr Ser
            340                 345                 350 gga ttc cag agt gag aac cat tcc cag aaa tgg atc ttg gga gat gtg      1104
Gly Phe Gln Ser Glu Asn His Ser Gln Lys Trp Ile Leu Gly Asp Val
            355                 360                 365 ttc att cgt gag tac tac agc gtc ttt gac agg gcc aac aac ctc gtt      1152
Phe Ile Arg Glu Tyr Tyr Ser Val Phe Asp Arg Ala Asn Asn Leu Val
    370                 375                 380 ggg cta gct aaa gca atc tga                                          1173
Gly Leu Ala Lys Ala Ile
385                 390

<210> SEQ ID NO 2
<211> LENGTH: 390
<212> TYPE: PRT
<213> ORGANISM: Bovine
```

-continued

<400> SEQUENCE: 2

```
Met Asn Phe Leu Lys Ser Phe Pro Phe Tyr Ala Phe Leu Cys Phe Gly
 1               5                  10                  15

Gln Tyr Phe Val Ala Val Thr His Ala Ala Glu Ile Thr Arg Ile Pro
             20                  25                  30

Leu Tyr Lys Gly Lys Ser Leu Arg Lys Ala Leu Lys Glu His Gly Leu
         35                  40                  45

Leu Glu Asp Phe Leu Gln Lys Gln Gln Tyr Gly Ile Ser Ser Lys Tyr
     50                  55                  60

Ser Gly Phe Gly Glu Val Ala Ser Val Pro Leu Thr Asn Tyr Leu Asp
 65                  70                  75                  80

Ser Gln Tyr Phe Gly Lys Ile Tyr Leu Gly Thr Pro Pro Gln Glu Phe
                 85                  90                  95

Thr Val Leu Phe Asp Thr Gly Ser Ser Asp Phe Trp Val Pro Ser Ile
            100                 105                 110

Tyr Cys Lys Ser Asn Ala Cys Lys Asn His Gln Arg Phe Asp Pro Arg
        115                 120                 125

Lys Ser Ser Thr Phe Gln Asn Leu Gly Lys Pro Leu Ser Ile His Tyr
    130                 135                 140

Gly Thr Gly Ser Met Gln Gly Ile Leu Gly Tyr Asp Thr Val Thr Val
145                 150                 155                 160

Ser Asn Ile Val Asp Ile Gln Gln Thr Val Gly Leu Ser Thr Gln Glu
                165                 170                 175

Pro Gly Asp Val Phe Thr Tyr Ala Glu Phe Asp Gly Ile Leu Gly Met
            180                 185                 190

Ala Tyr Pro Ser Leu Ala Ser Glu Tyr Ser Ile Pro Val Phe Asp Asn
        195                 200                 205

Met Met Asn Arg His Leu Val Ala Gln Asp Leu Phe Ser Val Tyr Met
    210                 215                 220

Asp Arg Asn Gly Gln Glu Ser Met Leu Thr Leu Gly Ala Ile Asp Pro
225                 230                 235                 240

Ser Tyr Tyr Thr Gly Ser Leu His Trp Val Pro Val Thr Val Gln Gln
                245                 250                 255

Tyr Trp Gln Phe Thr Val Asp Ser Val Thr Ile Ser Gly Val Val Val
            260                 265                 270

Ala Cys Glu Gly Gly Cys Gln Ala Ile Leu Asp Thr Gly Thr Ser Lys
        275                 280                 285

Leu Val Gly Pro Ser Ser Asp Ile Leu Asn Ile Gln Gln Ala Ile Gly
    290                 295                 300

Ala Thr Gln Asn Gln Tyr Gly Glu Phe Asp Ile Asp Cys Asp Asn Leu
305                 310                 315                 320

Ser Tyr Met Pro Thr Val Val Phe Glu Ile Asn Gly Lys Met Tyr Pro
                325                 330                 335

Leu Thr Pro Ser Ala Tyr Thr Ser Gln Asp Gln Gly Phe Cys Thr Ser
            340                 345                 350

Gly Phe Gln Ser Glu Asn His Ser Gln Lys Trp Ile Leu Gly Asp Val
        355                 360                 365

Phe Ile Arg Glu Tyr Tyr Ser Val Phe Asp Arg Ala Asn Asn Leu Val
    370                 375                 380

Gly Leu Ala Lys Ala Ile
385                 390
```

<210> SEQ ID NO 3
<211> LENGTH: 3957
<212> TYPE: DNA
<213> ORGANISM: Artificial Sequence
<220> FEATURE:
<221> NAME/KEY: CDS
<222> LOCATION: (1554)..(2726)
<223> OTHER INFORMATION: Description of Artificial Sequence: Phaseolin promoter- pre-pro- chymosin-phaseolin terminator

<400> SEQUENCE: 3

```
ctgcaggaat tcattgtact cccagtatca ttatagtgaa agttttggct ctctcgccgg      60
tggtttttta cctctattta aaggggtttt ccacctaaaa attctggtat cattctcact     120
ttacttgtta ctttaatttc tcataatctt tggttgaaat tatcacgctt ccgcacacga     180
tatccctaca aatttattat ttgttaaaca ttttcaaacc gcataaaatt ttatgaagtc     240
ccgtctatct ttaatgtagt ctaacatttt catattgaaa tatataattt acttaatttt     300
agcgttggta gaaagcataa agattttattc ttattcttct tcatataaat gtttaatata     360
caatataaac aaattcttta ccttaagaag gatttcccat tttatatttt aaaaatatat     420
ttatcaaata tttttcaacc acgtaaatct cataataata agttgtttca aaagtaataa     480
aatttaactc cataattttt ttattcgact gatcttaaag caacacccag tgacacaact     540
agccattttt ttctttgaat aaaaaaatcc aattatcatt gtattttttt tatacaatga     600
aaatttcacc aaacaatcat ttgtggtatt tctgaagcaa gtcatgttat gcaaaattct     660
ataattccca tttgacacta cggaagtaac tgaagatctg cttttacatg cgagacacat     720
cttctaaagt aattttaata atagttacta tattcaagat ttcatatatc aaatactcaa     780
tattacttct aaaaaattaa ttagatataa ttaaaatatt actttttaa ttttaagttt     840 aattgttgaa tttgtgacta ttgatttatt attctactat gtttaaattg ttttatagat     900
agtttaaagt aaatataagt aatgtagtag agtgttagag tgttacccta aaccataaac     960
tataacattt atggtggact aattttcata tatttcttat tgcttttacc ttttcttggt    1020
atgtaagtcc gtaactagaa ttacagtggg ttgccatggc actctgtggt cttttggttc    1080
atgcatgggt cttgcgcaag aaaaagacaa agaacaaaga aaaagacaa acagagaga    1140 caaaacgcaa tcacacaacc aactcaaatt agtcactggc tgatcaagat cgccgcgtcc    1200
atgtatgtct aaatgccatg caaagcaaca cgtgcttaac atgcacttta aatggctcac    1260
ccatctcaac ccacacacaa acacattgcc tttttcttca tcatccaccac aaccacctgt    1320 atatattcat tctcttccgc cacctcaatt tcttcacttc aacacacgtc aacctgcata    1380
tgcgtgtcat cccatgccca aatctccatg catgttccaa ccaccttctc tcttatataa    1440
tacctataaa tacctctaat atcactcact tctttcatca tccatccatc cagagtacta    1500
ctactctact actataatac cccaacccaa ctcatattca atactactct act atg       1556
                                                              Met
                                                                1 aac ttc ctt aag tct ttc cct ttc tac gct ttc ctt tgt ttc ggt caa     1604
Asn Phe Leu Lys Ser Phe Pro Phe Tyr Ala Phe Leu Cys Phe Gly Gln
        5                  10                  15 tac ttc gtt gct gtt act cac gct gct gag atc acc cgc att cct ctc     1652
Tyr Phe Val Ala Val Thr His Ala Ala Glu Ile Thr Arg Ile Pro Leu
    20                  25                  30 tac aaa ggt aag tct ctc cgt aag gcg ctg aag gaa cat gga ctt cta     1700
Tyr Lys Gly Lys Ser Leu Arg Lys Ala Leu Lys Glu His Gly Leu Leu
35                  40                  45
```

```
gaa gac ttc ttg cag aaa caa cag tat ggc atc agc agc aag tac tcc       1748
Glu Asp Phe Leu Gln Lys Gln Gln Tyr Gly Ile Ser Ser Lys Tyr Ser
 50              55                  60                  65 ggc ttc ggt gaa gtt gct agc gtg cca ctt acc aac tac ctt gat agt       1796
Gly Phe Gly Glu Val Ala Ser Val Pro Leu Thr Asn Tyr Leu Asp Ser
             70                  75                  80 caa tac ttt ggg aag atc tac ctc gga acc ccg cct caa gag ttc acc       1844
Gln Tyr Phe Gly Lys Ile Tyr Leu Gly Thr Pro Pro Gln Glu Phe Thr
         85                  90                  95 gtt ctc ttt gat act ggt tcc tct gac ttc tgg gtt ccc tct atc tac       1892
Val Leu Phe Asp Thr Gly Ser Ser Asp Phe Trp Val Pro Ser Ile Tyr
    100                 105                 110 tgc aag agc aat gcc tgc aag aac cac caa aga ttc gat ccg aga aag       1940
Cys Lys Ser Asn Ala Cys Lys Asn His Gln Arg Phe Asp Pro Arg Lys
115                 120                 125 tcg tcc acc ttc cag aac tta ggc aaa ccc ttg tct ata cac tac ggt       1988
Ser Ser Thr Phe Gln Asn Leu Gly Lys Pro Leu Ser Ile His Tyr Gly
130                 135                 140                 145 aca ggt agc atg caa gga atc tta ggc tat gat acc gtc act gtc tcc       2036
Thr Gly Ser Met Gln Gly Ile Leu Gly Tyr Asp Thr Val Thr Val Ser
                150                 155                 160 aac att gtg gac att caa cag aca gta gga ctt agc acc caa gaa cca       2084
Asn Ile Val Asp Ile Gln Gln Thr Val Gly Leu Ser Thr Gln Glu Pro
            165                 170                 175 ggt gat gtc ttc acc tat gca gaa ttc gat ggc atc ctt ggt atg gca       2132
Gly Asp Val Phe Thr Tyr Ala Glu Phe Asp Gly Ile Leu Gly Met Ala
        180                 185                 190 tac cca tcg ctc gcg tca gag tac tcg ata cct gtg ttt gac aac atg       2180
Tyr Pro Ser Leu Ala Ser Glu Tyr Ser Ile Pro Val Phe Asp Asn Met
    195                 200                 205 atg aac cga cac cta gta gct caa gac ttg ttc tcg gtt tac atg gac       2228
Met Asn Arg His Leu Val Ala Gln Asp Leu Phe Ser Val Tyr Met Asp
210                 215                 220                 225 agg aat ggc cag gag agc atg ctc acg ctt gga gct att gat cca tcc       2276
Arg Asn Gly Gln Glu Ser Met Leu Thr Leu Gly Ala Ile Asp Pro Ser
                230                 235                 240 tac tac aca gga tct ctt cac tgg gtt cca gtc act gtg cag cag tac       2324
Tyr Tyr Thr Gly Ser Leu His Trp Val Pro Val Thr Val Gln Gln Tyr
            245                 250                 255 tgg caa ttc act gtg gac agt gtc acc atc agc ggt gtg gtt gtt gca       2372
Trp Gln Phe Thr Val Asp Ser Val Thr Ile Ser Gly Val Val Val Ala
        260                 265                 270 tgt gaa ggt gga tgt caa gct atc ttg gat acc ggt acg tcc aag ctg       2420
Cys Glu Gly Gly Cys Gln Ala Ile Leu Asp Thr Gly Thr Ser Lys Leu
275                 280                 285 gtc gga cct agc agc gac att ctc aac att cag caa gct att gga gcc       2468
Val Gly Pro Ser Ser Asp Ile Leu Asn Ile Gln Gln Ala Ile Gly Ala
                290                 295                 300                 305 aca cag aac cag tac ggt gag ttt gac ata gat tgc gac aac ctt agc       2516
Thr Gln Asn Gln Tyr Gly Glu Phe Asp Ile Asp Cys Asp Asn Leu Ser
            310                 315                 320 tac atg cct aca gtt gtc ttt gag atc aac ggc aag atg tac cca ctg       2564
Tyr Met Pro Thr Val Val Phe Glu Ile Asn Gly Lys Met Tyr Pro Leu
        325                 330                 335 acc ccc tcc gcc tat acc agc cag gat caa ggg ttc tgc acc agt gga       2612
Thr Pro Ser Ala Tyr Thr Ser Gln Asp Gln Gly Phe Cys Thr Ser Gly
    340                 345                 350 ttc cag agt gag aac cat tcc cag aaa tgg atc ttg gga gat gtg ttc       2660
Phe Gln Ser Glu Asn His Ser Gln Lys Trp Ile Leu Gly Asp Val Phe
355                 360                 365
```

-continued

```
att cgt gag tac tac agc gtc ttt gac agg gcc aac aac ctc gtt ggg    2708
Ile Arg Glu Tyr Tyr Ser Val Phe Asp Arg Ala Asn Asn Leu Val Gly
370                 375                 380                 385 cta gct aaa gca atc tga agcttaataa gtatgaacta aaatgcatgt           2756
Leu Ala Lys Ala Ile
                390 aggtgtaaga gctcatggag agcatggaat attgtatccg accatgtaac agtataataa  2816
ctgagctcca tctcacttct tctatgaata acaaaggat gttatgatat attaacactc   2876
tatctatgca ccttattgtt ctatgataaa tttcctctta ttattataaa tcatctgaat  2936
cgtgacggct tatggaatgc ttcaaatagt acaaaaacaa atgtgtacta taagactttc  2996
taaacaattc taactttagc attgtgaacg agacataagt gttaagaaga cataacaatt  3056
ataatggaag aagtttgtct ccatttatat attatatatt acccactat gtattatatt   3116
aggatgttaa ggagacataa caattataaa gagagaagtt tgtatccatt tatatattat  3176
atactaccca tttatatatt atacttatcc acttatttaa tgtctttata aggtttgatc  3236
catgatattt ctaatatttt agttgatatg tatatgaaag ggtactattt gaactctctt  3296
actctgtata aaggttggat catccttaaa gtgggtctat ttaattttat tgcttcttac  3356
agataaaaaa aaaattatga gttggtttga taaaatattg aaggatttaa ataataata   3416
aataataaat aacatataat atatgtatat aaatttatta taatataaca tttatctata  3476
aaaaagtaaa tattgtcata aatctataca atcgtttagc cttgctggac gactctcaat  3536
tatttaaacg agagtaaaca tatttgactt tttggttatt taacaaatta ttatttaaca  3596
ctatatgaaa ttttttttt ttatcggcaa ggaaataaaa ttaaattagg agggacaatg   3656
gtgtgtccca atccttatac aaccaacttc cacaggaagg tcaggtcggg gacaacaaaa  3716
aaacaggcaa gggaaatttt ttaatttggg ttgtcttgtt tgctgcataa tttatgcagt  3776
aaaacactac acataaccct tttagcagta gagcaatggt tgaccgtgtg cttagcttct  3836
tttatttat tttttatca gcaaagaata aataaaataa aatgagacac ttcagggatg   3896
tttcaacccct tatacaaaac cccaaaaaca agtttcctag caccctacca actaaggtac  3956
c                                                                 3957
```

<210> SEQ ID NO 4
<211> LENGTH: 390
<212> TYPE: PRT
<213> ORGANISM: Artificial Sequence
<220> FEATURE:
<223> OTHER INFORMATION: Description of Artificial Sequence: Phaseolin
    promoter- pre-pro- chymosin-phaseolin terminator

<400> SEQUENCE: 4

```
Met Asn Phe Leu Lys Ser Phe Pro Phe Tyr Ala Phe Leu Cys Phe Gly
 1               5                  10                  15

Gln Tyr Phe Val Ala Val Thr His Ala Ala Glu Ile Thr Arg Ile Pro
                20                  25                  30

Leu Tyr Lys Gly Lys Ser Leu Arg Lys Ala Leu Lys Glu His Gly Leu
            35                  40                  45

Leu Glu Asp Phe Leu Gln Lys Gln Gln Tyr Gly Ile Ser Ser Lys Tyr
        50                  55                  60

Ser Gly Phe Gly Glu Val Ala Ser Val Pro Leu Thr Asn Tyr Leu Asp
 65                 70                  75                  80

Ser Gln Tyr Phe Gly Lys Ile Tyr Leu Gly Thr Pro Pro Gln Glu Phe
                85                  90                  95
```

```
                    -continued

Thr Val Leu Phe Asp Thr Gly Ser Ser Asp Phe Trp Val Pro Ser Ile
            100                 105                 110

Tyr Cys Lys Ser Asn Ala Cys Lys Asn His Gln Arg Phe Asp Pro Arg
            115                 120                 125

Lys Ser Ser Thr Phe Gln Asn Leu Gly Lys Pro Leu Ser Ile His Tyr
            130                 135                 140

Gly Thr Gly Ser Met Gln Gly Ile Leu Gly Tyr Asp Thr Val Thr Val
145                 150                 155                 160

Ser Asn Ile Val Asp Ile Gln Gln Thr Val Gly Leu Ser Thr Gln Glu
                165                 170                 175

Pro Gly Asp Val Phe Thr Tyr Ala Glu Phe Asp Gly Ile Leu Gly Met
                180                 185                 190

Ala Tyr Pro Ser Leu Ala Ser Glu Tyr Ser Ile Pro Val Phe Asp Asn
            195                 200                 205

Met Met Asn Arg His Leu Val Ala Gln Asp Leu Phe Ser Val Tyr Met
        210                 215                 220

Asp Arg Asn Gly Gln Glu Ser Met Leu Thr Leu Gly Ala Ile Asp Pro
225                 230                 235                 240

Ser Tyr Tyr Thr Gly Ser Leu His Trp Val Pro Val Thr Val Gln Gln
            245                 250                 255

Tyr Trp Gln Phe Thr Val Asp Ser Val Thr Ile Ser Gly Val Val Val
            260                 265                 270

Ala Cys Glu Gly Gly Cys Gln Ala Ile Leu Asp Thr Gly Thr Ser Lys
            275                 280                 285

Leu Val Gly Pro Ser Ser Asp Ile Leu Asn Ile Gln Gln Ala Ile Gly
        290                 295                 300

Ala Thr Gln Asn Gln Tyr Gly Glu Phe Asp Ile Asp Cys Asp Asn Leu
305                 310                 315                 320

Ser Tyr Met Pro Thr Val Val Phe Glu Ile Asn Gly Lys Met Tyr Pro
            325                 330                 335

Leu Thr Pro Ser Ala Tyr Thr Ser Gln Asp Gln Gly Phe Cys Thr Ser
            340                 345                 350

Gly Phe Gln Ser Glu Asn His Ser Gln Lys Trp Ile Leu Gly Asp Val
            355                 360                 365

Phe Ile Arg Glu Tyr Tyr Ser Val Phe Asp Arg Ala Asn Asn Leu Val
        370                 375                 380

Gly Leu Ala Lys Ala Ile
385                 390
```